(12) United States Patent
Dilmanian et al.

(10) Patent No.: US 10,124,194 B2
(45) Date of Patent: Nov. 13, 2018

(54) RADIATION THERAPY WITH ORTHOVOLTAGE X-RAY MINIBEAMS

(71) Applicant: The Research Foundation for State University of New York, Albany, NY (US)

(72) Inventors: F. Avraham Dilmanian, Yaphank, NY (US); Sunil Krishnan, Houston, TX (US); John Gordon Eley, Baltimore, MD (US)

(73) Assignees: The Research Foundation for State University of New York, Albany, NY (US); The Board of Regents, The University of Texas System, Austin, TX (US)

( * ) Notice: Subject to any disclaimer, the term of this patent is extended or adjusted under 35 U.S.C. 154(b) by 189 days.

(21) Appl. No.: 15/188,643

(22) Filed: Jun. 21, 2016

(65) Prior Publication Data
US 2017/0036043 A1 Feb. 9, 2017

Related U.S. Application Data

(60) Provisional application No. 62/201,247, filed on Aug. 5, 2015, provisional application No. 62/210,623, filed (Continued)

(51) Int. Cl.
*A61N 5/10* (2006.01)
*A61B 6/06* (2006.01)

(52) U.S. Cl.
CPC .............. *A61N 5/1084* (2013.01); *A61B 6/06* (2013.01); *A61N 2005/1091* (2013.01); *A61N 2005/1098* (2013.01)

(58) Field of Classification Search
CPC .......... A61N 5/1084; A61N 2005/1098; A61N 2005/1091; A61B 6/06
(Continued)

(56) References Cited

U.S. PATENT DOCUMENTS 6,714,627 B1 * 3/2004 Brown ................. A61N 5/1042
378/152
7,158,607 B2 1/2007 Dilmanian et al.
(Continued)

OTHER PUBLICATIONS

Int'l Search Report &Written Opinion, US Int'l Searching Authority, Application Ser. No. PCT/US2016/042903, dated Sep. 28, 2016.
(Continued)

*Primary Examiner* — Courtney Thomas
(74) *Attorney, Agent, or Firm* — Betsy Kingsbury Dowd; BKDowd Law, P.C.

(57) ABSTRACT

A method for delivering therapeutic radiation to a target includes positioning a multi-aperture collimator on the skin within a trajectory of orthovoltage x-rays directed at the target, thus generating an array of minibeams, each of width between 0.1 mm to 0.6 mm. The skin is irradiated with the array. An effective beam of therapeutic radiation, which may be a solid beam, is delivered to the target at a predetermined tissue depth by merging adjacent orthovoltage x-ray minibeams sufficiently to form the effective beam. The effective beam may be formed proximal to the target. The depth at which the effective, preferably, solid, beam is formed is controlled by varying one or more of the spacing of the minibeams in the array, the minibeam width, the distance from the x-ray source to the collimator, and the x-ray source spot size. Planar minibeams can be arc-scanned while continuously modulating beam shape and intensity.

43 Claims, 15 Drawing Sheets

Related U.S. Application Data on Aug. 27, 2015, provisional application No. 62/311,325, filed on Mar. 21, 2016.

(58) Field of Classification Search
USPC .......................................................... 378/65
See application file for complete search history.

(56) References Cited

U.S. PATENT DOCUMENTS

| | | | | |
|---|---|---|---|---|
| 7,194,063 B2* | 3/2007 | Dilmanian | ........... | A61N 5/1042 378/64 |
| 7,490,982 B2* | 2/2009 | Gregerson | ............. | A61B 6/032 378/193 |
| 7,620,147 B2* | 11/2009 | Gertner | .................... | A61N 5/10 378/145 |
| 2004/0047804 A1* | 3/2004 | Wolf | .................. | A61K 41/0038 424/1.11 |

OTHER PUBLICATIONS

Harris W., Recent clinical experience with the grid in the x-ray treatment of advanced cancer; preliminary report. Radiology. Mar. 1952;58(3):343-50.

\* cited by examiner

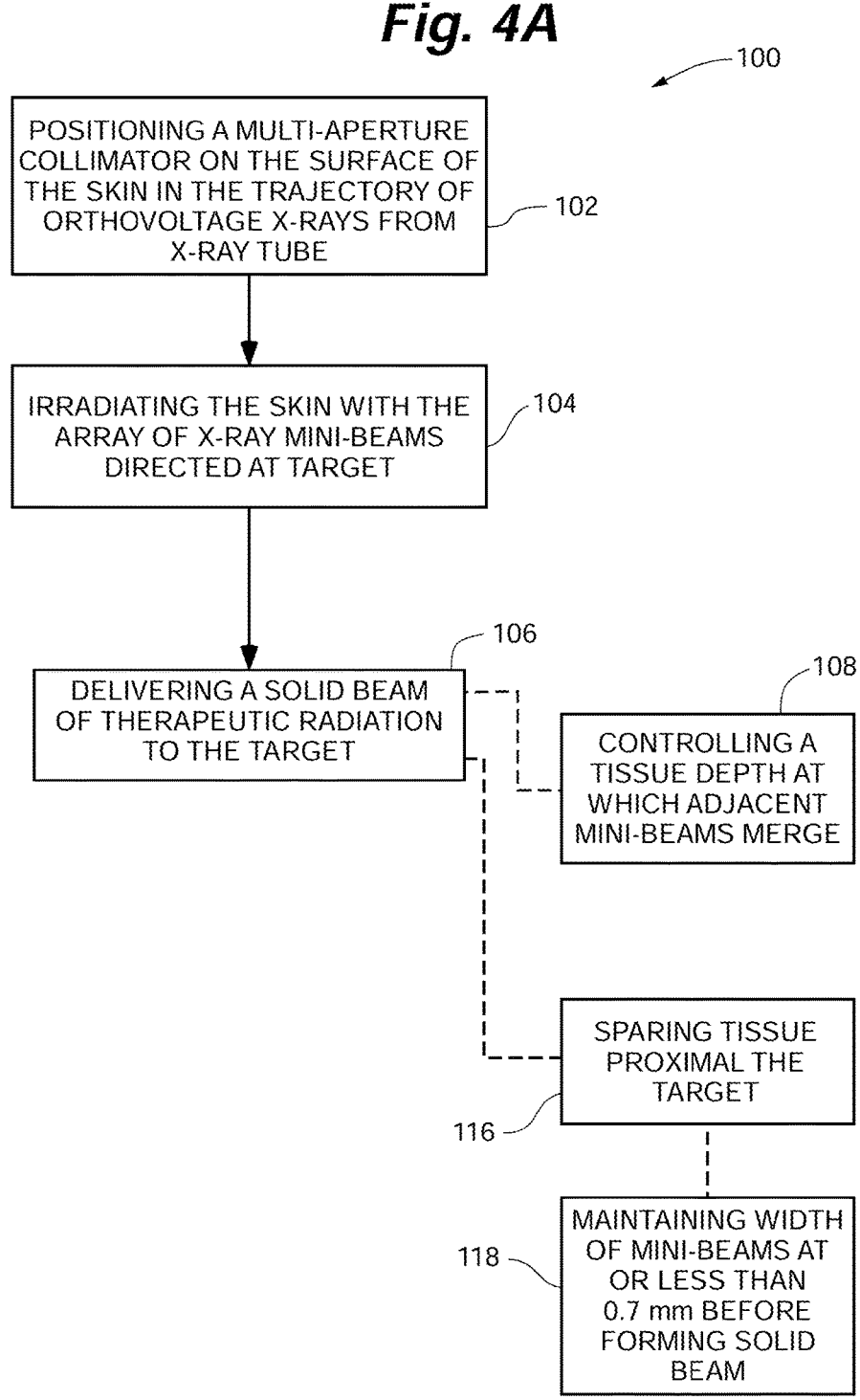

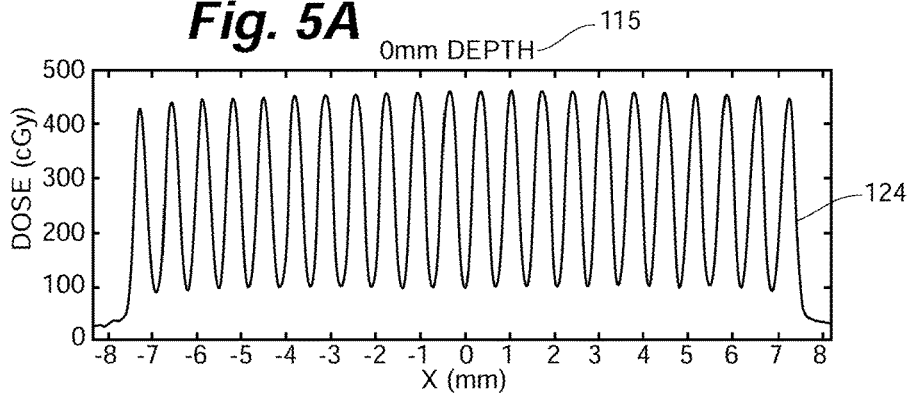
Fig. 5A 0mm DEPTH
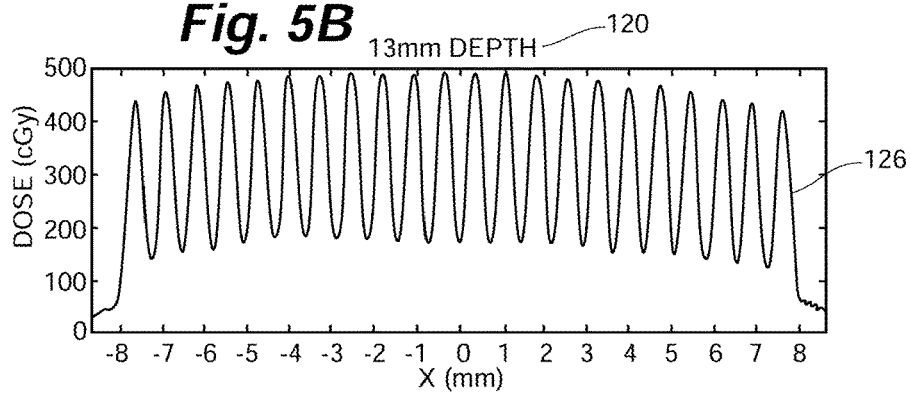
Fig. 5B 13mm DEPTH
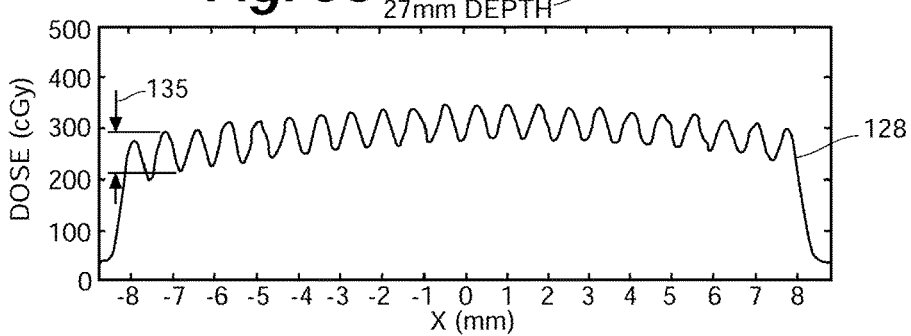
Fig. 5C 27mm DEPTH
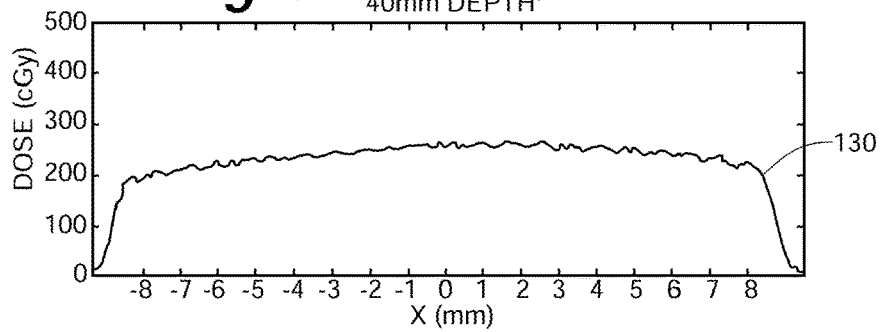
Fig. 5D 40mm DEPTH

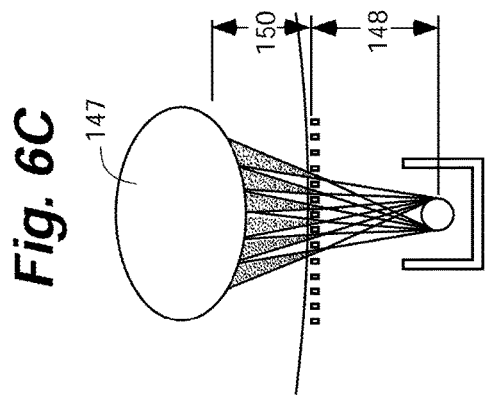
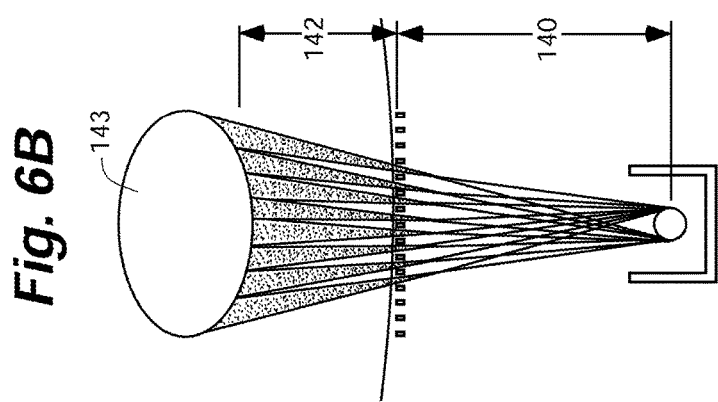
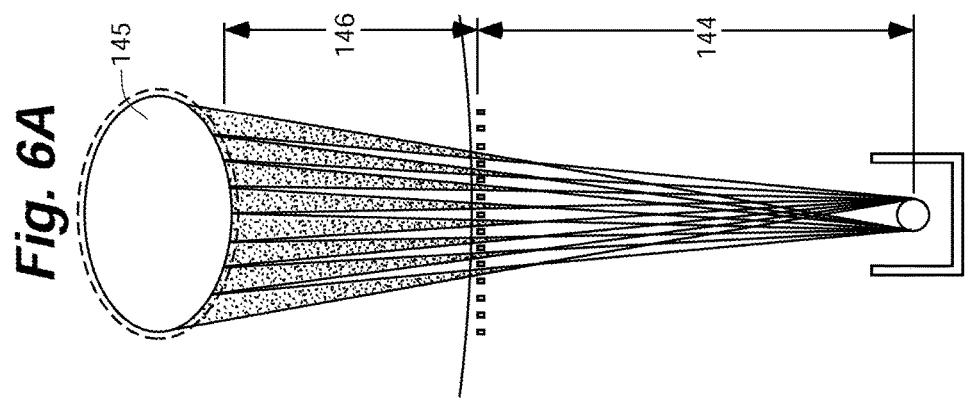

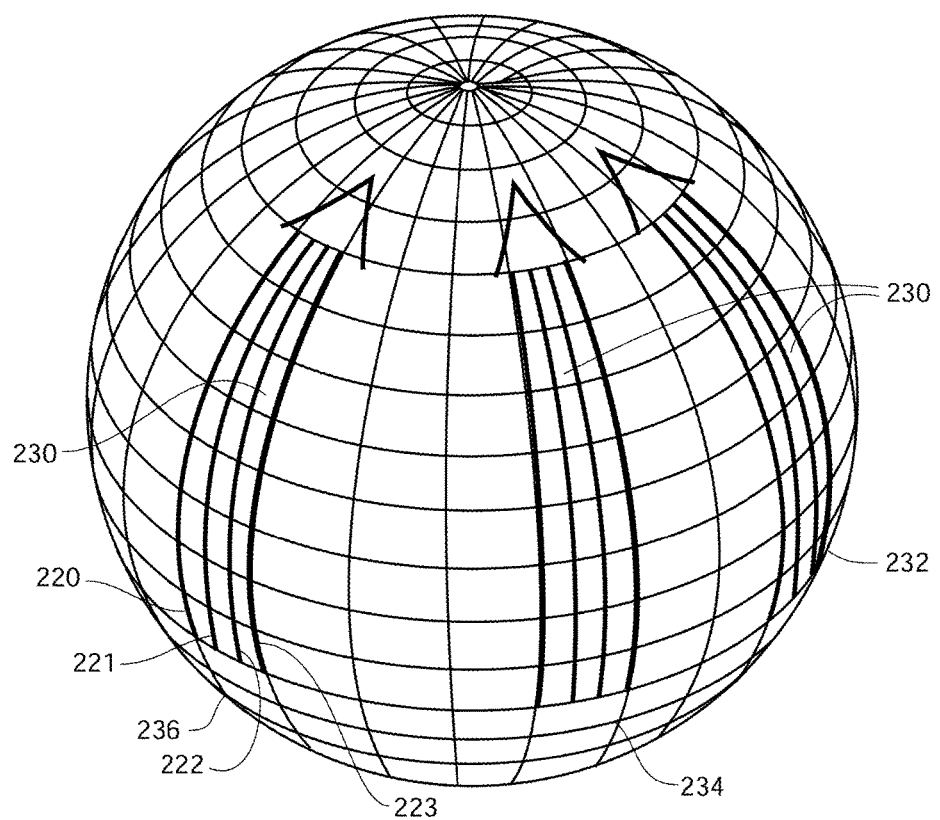

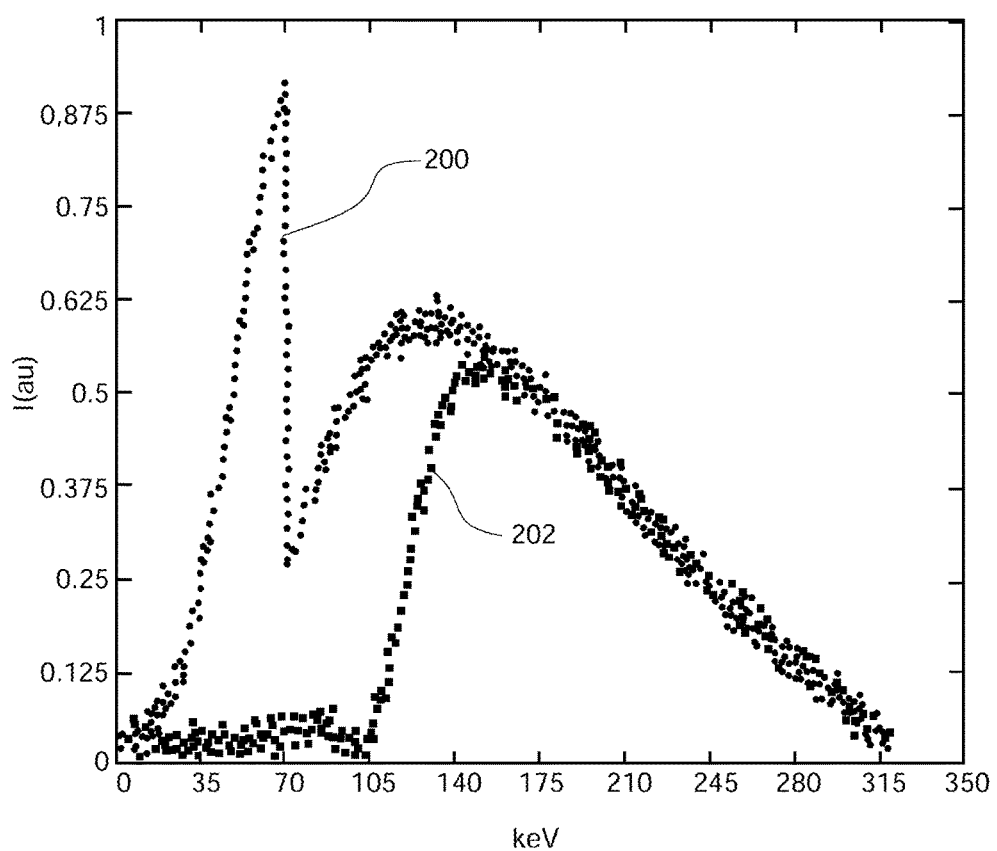

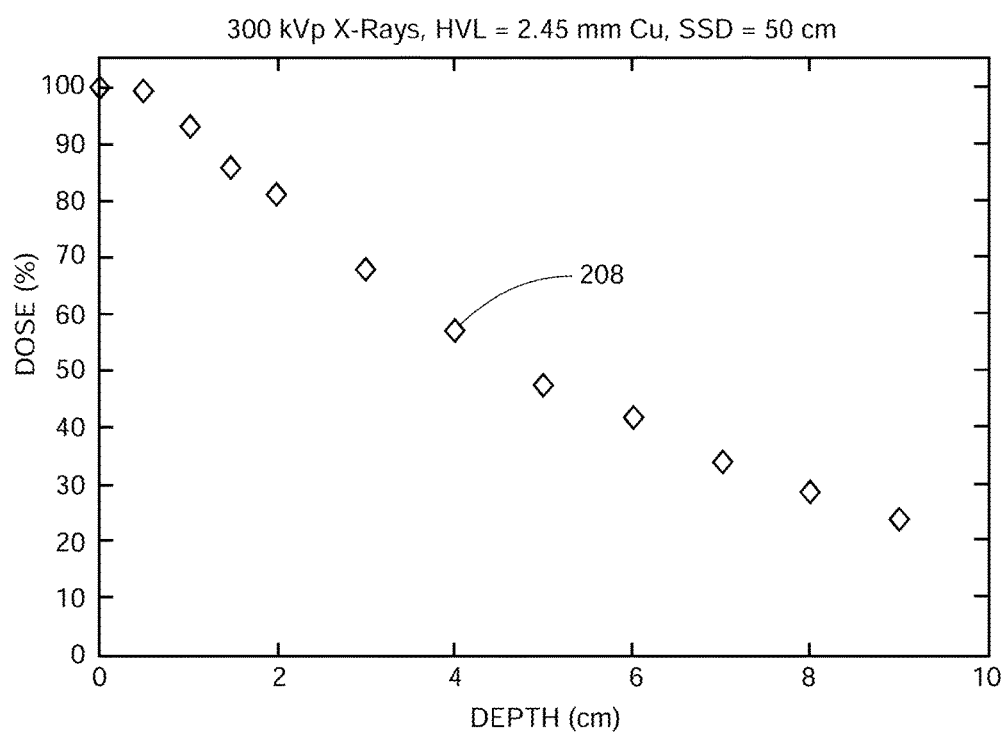

RADIATION THERAPY WITH ORTHOVOLTAGE X-RAY MINIBEAMS

CROSS-REFERENCE TO RELATED APPLICATIONS

This application claims the benefit of and priority to U.S. Provisional Application Ser. No. 62/201,247, filed Aug. 5, 2015, entitled "Orthovoltage X-Ray Collimator and Radiation Therapy Utilizing Same," U.S. Provisional Application Ser. No. 62/210,623, filed Aug. 27, 2015, entitled "Orthovoltage X-Ray Minibeams: Radiation Therapy With Smaller Impact on Non-targeted Tissues," and U.S. Provisional Application Ser. No. 62/311,325, filed Mar. 21, 2016, entitled "Arc-Scan Intensity-Modulated Radiation Therapy Using Orthovoltage X-Ray Minibeams," the entirety of each of which is hereby incorporated herein by reference thereto.

FIELD OF THE DISCLOSURE

The present disclosure relates to methods and systems for performing radiation therapy using orthovoltage x-rays for treating tumors, including brain tumors, and for treating neurological disorders such as epilepsy.

BACKGROUND

Radiation therapy, which is one of three main methods of treating cancer, together with surgery and chemotherapy, is currently carried out predominantly with high energy x-rays of one to several MeV energy produced by special x-ray generators employing electron linear accelerators ("linacs") of several MV high voltage. MeV x-rays have good attributes for use in radiation therapy, in particular, high tissue penetration and a robust sparing of the first few millimeters of shallow tissues, generally known as a "skin-sparing effect." They also have several shortcomings, most significantly, the normal, non-targeted tissue that is located proximal, distal, and lateral to the target receive excessive radiation damage as described further herein.

This is because the mode of interaction of the high energy x-rays that are produced, typically 1-4 MeV, is Compton scattering and not photoelectric. As a result, the dose distribution produced in a patient's body is mostly from multiple Compton scattering from a wide range of angles and, therefore, is not well-confined within the target.

In particular, the doses produced at the target tissue by MV sources do not sharply fall at the target's edge. Instead, the dose distribution at the target's edge is rather blunt-edged. Quantitatively, the so-called "80%-to-20% dose fall-off" produced at the target by high energy x-rays is typically 2-5 mm. In addition, the beam-shaping collimators, so-called "multi-leaf collimators," required to produce the high-energy beam profiles, consist of heavy, thick "leaves" which do not lend themselves to production of fine exposure profiles. Because these collimators fail to produce beam-exposure profiles with fine contours, unnecessary radiation dose is delivered to normal tissues, especially when small targets are exposed. Such large falloffs result in unnecessary and undesirable dose being delivered to the tissues located in the immediate neighborhood of the target.

Further, because high energy x-rays have little preferential absorption in heavier elements compared to the light elements that constitute most of the tissues, the concept of tumor-dose enhancement by the introduction of contrast agents to the tumor such as iodine and gold cannot be effectively implemented when the radiation type is high energy x-rays. In addition, although the large penetration of the dose from high-energy x-rays to tissue depths is considered an advantage for thick targets, for thin tumors the shallow dose falloff of the high energy x-rays with depth is a negative effect, allowing the exposure to high radiation dose of all tissues positioned distal to the target. FIG. 1 illustrates dose penetration 10 in tissues for different high-energy MeV x-ray beams 12, compared to the dose penetration curve for an orthovoltage tube 14.

Before MV x-ray machines were developed (around the mid-20th century), x-ray generators of lower energy, called "orthovoltage" x-ray machines or tubes were used for radiation therapy. The acceleration voltage of these early x-ray machines was rather small, mostly up to 250 kVp, producing x-rays with a median energy, or mean energy, of about 110 keV. These beam energies were too low to penetrate deep in the tissue, and also lacked the beam sparing effect of the shallow tissues that the high-energy MV x-rays exhibit, in fact lower than that shown in FIG. 1 for orthovoltage x-rays. As a result, the skin and the normal tissues proximal to the target received significant radiation damage. FIG. 1 compares the dose penetration in tissues from high energy x-rays produced by electron linacs to that from a 300 kVp orthovoltage tube filtered moderately, labeled by half-value layer (HVL) in copper as "3.0 mm Cu HVL."

To address the damage to healthy skin tissue using orthovoltage x-rays, a so-called "grid therapy" was developed. Conventional grid therapy used a metal or lead grid with openings of at least 1.0-1.5 cm diameter to ameliorate the skin damage that occurred in treating deep tumors. However, the orthovoltage grid therapy techniques offered little, if any, tissue-sparing to healthy subcutaneous tissue proximal to the target, and thus did not solve the problem of damage to the normal tissues proximal to deep tumors. Furthermore, no method or system was contemplated for controlling the tissue depth at which a therapeutic dose could be produced across a target by the merging of the beams exiting the grid.

Accordingly, there is a need for a method and system for performing radiotherapy using orthovoltage x-rays for effectively treating tumors while sparing both the skin and tissue proximal to the target. There is also a need for a system and method for controlling the tissue depth at which a therapeutic dose of orthovoltage x-ray radiation can be delivered to the target while sparing tissue proximal to the target. The development of such improved orthovoltage x-ray systems may provide not only benefit to a wide range of clinical applications by reducing dose to the non-targeted tissues, but also a low-cost and compact solution for performing radiotherapy to effectively treat tumors, as well as neurological targets.

SUMMARY

Features of the disclosure will become apparent from the following detailed description considered in conjunction with the accompanying drawings. It is to be understood, however, that the drawings are designed as an illustration only and not as a definition of the limits of this disclosure.

The present disclosure relates to a system and method for effectively treating tumors and neurological targets using orthovoltage x-ray radiation while sparing both the skin and irradiated tissue that is proximal to the target. The present disclosure also relates to a system and method for controlling the tissue depth at which a therapeutic dose of orthovoltage x-ray radiation can be delivered to the target while sparing at least a substantial portion of tissue proximal to the target. Such improved orthovoltage x-ray systems may provide a low-cost and compact solution for performing radiotherapy to effectively treat tumors, as well as neurological targets.

The present disclosure also relates to a method for delivering therapeutic radiation to a target within a subject, wherein the target is located at a predetermined depth from an irradiated portion of a surface of the skin of the subject. The method includes positioning a multi-aperture collimator on or near the surface of the skin within a trajectory of radiation, which is produced by an x-ray source generating orthovoltage x-rays, and which is directed at the target. The multi-aperture collimator is positioned and configured to generate an array of minibeams on the surface of the skin comprising slightly diverging spatially distinct minibeams. Adjacent minibeams formed on the skin have a predetermined center-center spacing, and, preferably, a width of between about 0.1 mm and about 0.6 mm. The method further includes irradiating the surface of the skin with the array of minibeams, and delivering an effective beam of therapeutic radiation to the target by controlling a tissue depth at which adjacent orthovoltage x-ray minibeams merge sufficiently to form the effective beam of therapeutic radiation.

In one aspect, the method further includes controlling the tissue depth at which the adjacent orthovoltage x-ray minibeams merge sufficiently to form the effective beam such that the effective beam is formed proximal to the target.

The orthovoltage x-ray source may be a focal spot on an anode of an x-ray tube.

In aspects, controlling the tissue depth at which the adjacent minibeams merge sufficiently to form the effective beam includes adjusting at least one of the predetermined center-to-center spacing, the width, and a distance between the x-ray source and the multi-aperture collimator.

In various additional aspects, controlling the tissue depth at which the adjacent minibeams merge sufficiently to form the effective beam includes adjusting a size of the x-ray source from which the orthovoltage x-rays are generated.

The tissue depth can be varied, in aspects, from about 1 cm to about 10 cm, based on a predetermined depth of the target from the surface of the skin.

Controlling the tissue depth may include, in aspects, selecting the width, the predetermined center-to-center spacing, and the distance between the focal spot and the collimator such that each of the minibeams broaden to less than 1.0 mm in width before they merge to form the effective beam of therapeutic radiation, which may be a solid, or substantially solid, beam of therapeutic radiation.

In aspects, the multi-aperture collimator is a multi-slit collimator configured with elongated slits such that the array of minibeams is an array of narrow and elongated planar minibeams. In some aspects, the width, which corresponds to a thickness of each planar minibeam, may be limited to a range of between about 0.25 mm to about 0.35 mm.

The x-ray source, which may be a focal spot formed on the anode of an x-ray tube, may have an elongated shape in embodiments, and aspects of the method may further include aligning the elongated slits of the multi-slit collimator with the elongated shape of the focal spot.

In yet another aspect, delivering the beam of therapeutic radiation further includes sparing irradiated tissue proximal to the target from radiation damage, such that the tissue depth also corresponds to a tissue sparing depth.

In still other aspects, the method further includes changing an angular position of the x-ray tube and the trajectory of orthovoltage x-rays generated therefrom relative to the target such that the target is irradiated from a different direction, and a different portion of the skin is irradiated. The positioning, irradiating and delivering steps are repeated for the different direction. The multi-aperture collimator is repositioned for irradiating the different portion of the surface of the skin while remaining aligned with the trajectory of orthovoltage x-rays for the different direction. The irradiating step is repeated to irradiate the different portion of the skin with the array of minibeams generated by the multi-aperture collimator, and the delivering step is repeated to deliver the effective beam of therapeutic radiation to the target from the different direction.

For each angular position, the method, in aspects, also includes adjusting a beam-shaping collimator and an intensity of the beam to conform the effective beam to a shape of the target based on the direction of the trajectory relative to the target.

In still another aspect of the method, the radiating step includes generating an arc of radiation around the target from each of the minibeams in the array. The delivering step includes merging adjacent arcs of radiation at the tissue depth to form the effective beam of therapeutic radiation.

In aspects, the minibeams for forming the arcs of radiation may be planar minibeams, formed from elongated slits of a multi-slit collimator, having a length that is greater than the width, or thickness, of each minibeam.

The arcs of radiation can be generated by rotating the x-ray source together with the multi-aperture, e.g., a multi-slit collimator, such that the arcs are generated around the target in planes parallel to, for example, the elongated slits of a multi-slit collimator.

In aspects, while generating the arcs of radiation, the method further includes continuously adjusting a shape and an intensity of the beam to conform the effective beam of therapeutic radiation to a shape of the target based on a direction from which the beam irradiates the target.

The distance between the multi-aperture collimator and the x-ray source is also preferably continuously controlled and adjusted, based on the direction, to maintain the tissue depth at which the arcs formed from the minibeams merge to form the beam of therapeutic radiation to be proximal to the target.

Various aspects of the method may further include administering dose-enhancing agents to the subject prior to the irradiating step to radio-sensitize the target. The agents may be in various forms, including nanoparticles, and may include one or more of iodine, gadolinium, gold, and platinum. In aspects, the agents may be encapsulated in one of liposomes or polymeric delivery vehicles.

The present disclosure is also directed to a system for delivering therapeutic radiation to a target volume within a subject, wherein the target is located at a predetermined depth measured from an irradiated portion of the skin of the subject. The system includes an x-ray source generating orthovoltage x-rays and a multi-aperture collimator. The multi-aperture collimator is configured for positioning on the skin within a trajectory of the orthovoltage x-rays directed at the target. The multi-aperture collimator includes an array of apertures having a width of between about 0.1 mm and about 0.6 mm and a predetermined center-center spacing to generate an array of slightly diverging spatially distinct minibeams of the orthovoltage x-rays at the skin. The width and the predetermined center-center spacing of the multi-aperture collimator, a size of the x-ray source, and a distance between the x-ray source and the collimator are configured to deliver an effective beam of therapeutic radiation to the target, wherein the beam is formed by sufficient merging of the minibeams proximal to the target.

In aspects, the x-ray source is a focal spot on an anode of an orthovoltage x-ray tube from which orthovoltage x-rays are generated.

In one aspect, the effective beam of therapeutic radiation is a solid, or substantially solid, beam of therapeutic radiation. The width, the predetermined center-center spacing, the size of the x-ray source and the distance are configured to form the solid beam proximal to the target.

In another aspect, the multi-aperture collimator is removably interchangeable. The system further includes a set of multi-aperture collimators configured with predefined aperture widths and shapes and predefined center-center spacings.

In additional aspects, the system may be portable and configured to be transported on and operated from a mobile platform.

In aspects, the system further includes a beam-shaping collimator, positioned in the trajectory of the x-rays and proximal to the multi-aperture collimator, the beam-shaping collimator further configured to be adjustable to conform the effective beam of therapeutic radiation to a shape and size of the target.

The system may further include, in various aspects, a rotatable and translatable gantry on which the orthovoltage x-ray source, the beam-shaping collimator and the multi-aperture collimator are mounted, the gantry being positioned and configured to be rotatable around a horizontal platform on which a subject being treated is located. The gantry is configured to position the target in the trajectory of the orthovoltage x-rays, to tilt around a vertical axis to the platform to change a direction from which the target is irradiated with the effective beam of therapeutic radiation, and to rotate around a longitudinal axis of the horizontal platform to generate arcs of radiation from each of the minibeams.

In additional aspects, the system is further configured to continuously adjust the beam-shaping collimator to conform the effective beam to the shape and size of the target based on the direction of irradiation as the gantry is tilted and rotated, and to continuously adjust the distance between the x-ray source and the multi-aperture collimator to maintain the tissue depth at which the minibeams merge to be proximal to the target.

In various additional aspects of the system and method of the present disclosure, the width of the minibeams may be between about 0.25 mm and about 0.35 mm.

In other aspects of the system and method of the present disclosure, the minibeams may be pencil beams. In yet another aspect, the array may be a two-dimensional array of pencil beams.

The pencil beams of the present disclosure, in aspects, may have a cross-sectional profile that is round, elliptical, square, rectangular, or of polygonal shape.

In various other aspects of the system and method of the present disclosure, the multi-aperture collimator may be a multi-slit collimator configured with elongated slits such that the array of minibeams is an array of narrow and elongated planar minibeams.

The collimator may include a multi-aperture or multi-slit heavy-metal plate.

In various aspects, the width of the apertures, or slits, in the multi-aperture collimator is between about 0.25 mm and 0.35 mm.

The orthovoltage x-ray tube in various aspects may operate in a range between about 100 kVp and about 500 kVp.

The present disclosure is also directed to a method for delivering therapeutic radiation to a target within a subject, wherein the target is located at a predetermined depth, and the predetermined depth is measured from an irradiated portion of a surface of the skin of the subject. The method includes positioning a multi-aperture collimator within a trajectory of orthovoltage x-rays generated by an orthovoltage x-ray source. The trajectory of orthovoltage x-rays is directed at the target. The multi-aperture collimator is positioned and configured to generate an array of minibeams on the surface of the skin comprising slightly diverging spatially distinct minibeams having a predetermined width and a predetermined center-center spacing between adjacent minibeams.

The method also includes irradiating the surface of the skin with arcs of radiation formed from the array of minibeams, wherein the arcs of radiation are generated around the target from the minibeams in the array, and delivering an effective beam of therapeutic radiation to the target. The beam is delivered by controlling a tissue depth from the irradiated surface of the skin at which adjacent arcs of radiation formed from adjacent minibeams in the array merge sufficiently to form the effective beam of therapeutic radiation.

In aspects, the method further includes limiting the width of the minibeams to be between about 0.1 mm and about 0.6 mm.

In addition aspects, the minibeams are planar minibeams formed from elongated slits of a multi-slit collimator. The arcs of radiation are generated from the minibeams by rotating the x-ray source together with the multi-slit collimator, such that the arcs are generated around the target in planes parallel to the elongated slits of the multi-slit collimator.

The method may further include, in aspects, adjusting a shape and an intensity of the effective beam of therapeutic radiation to conform to a shape of the target based on a direction from which the beam irradiates the target.

In further aspects, the method also includes continuously adjusting the distance between the orthovoltage x-ray source and the multi-aperture collimator to maintain the tissue depth at which the minibeams forming the arcs of radiation merge to be proximal to the target.

The system and methods of the present disclosure may be applied, in aspects, to delivering a beam, which may, in additional aspects, be a solid beam, of therapeutic radiation to a target that encompasses one of a tumor and an epileptogenic foci.

In addition to the above aspects of the present disclosure, additional aspects, objects, features and advantages will be apparent from the embodiments presented in the following description and in connection with the accompanying drawings.

BRIEF DESCRIPTION OF THE DRAWINGS

The drawings constitute a part of this disclosure and include examples, which may be implemented in various forms. It is to be understood that in some instances, various aspects of the disclosure may be shown exaggerated or enlarged to facilitate understanding. The teaching of the disclosure can be readily understood by considering the following detailed description in conjunction with the accompanying drawings.

FIG. 4A is a block diagram representation of an embodiment of a method of the present embodiment.

FIGS. 5A to 5D are graphical representations of dose profiles, taken perpendicular to an orthovoltage x-ray minibeam array formed in accordance with the present disclosure, at incrementally increased depths.

FIGS. 6A to 6C are pictorial representations of the implementation of the system of FIG. 2A to different target depths in accordance with an embodiment of a method of the present disclosure.

FIG. 7B represents a geometry for forming arcs of radiation from an array of orthovoltage x-ray minibeams in accordance with an embodiment of a method of the present disclosure.

FIG. 9 is a graphical representation of the advantage of filtering an energy spectrum of an orthovoltage x-ray beam of the present disclosure to increase its median beam energy.

FIG. 10 is a graphical representation of the dose penetration achieved using orthovoltage x-ray minibeams formed in accordance with an embodiment of the system and method of the present disclosure.

Figure 1:
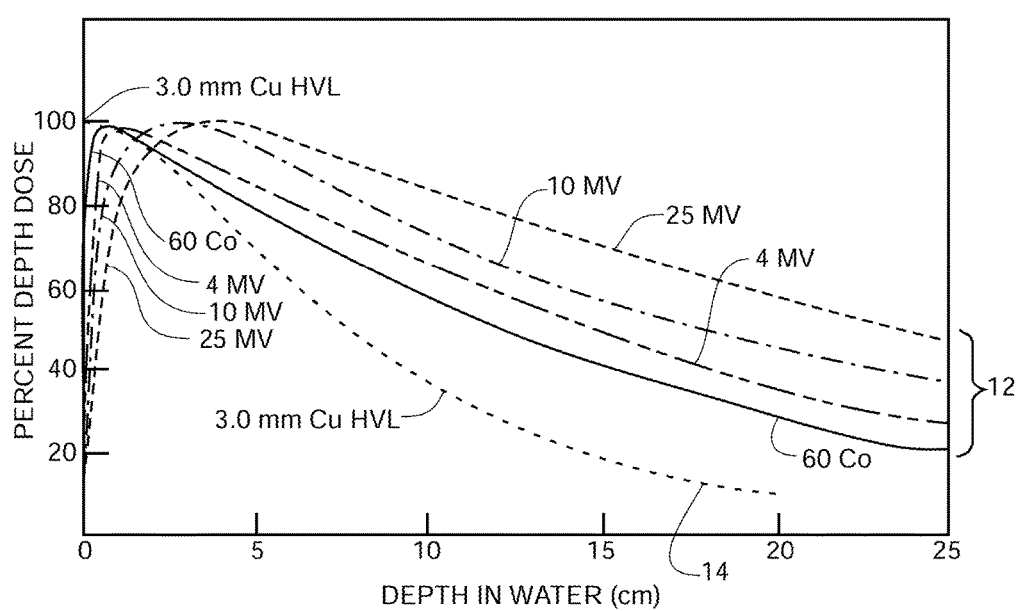
FIG. 1 is a graphic representation of dose penetration in water for different radiation sources.

The various aspects of the present disclosure mentioned above are described in further detail with reference to the aforementioned figures and the following detailed description of exemplary embodiments.

DETAILED DESCRIPTION

The following sections describe exemplary embodiments of the present disclosure. It should be apparent to those skilled in the art that the described embodiments of the present disclosure provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present disclosure as defined herein and equivalents thereto.

The present disclosure is directed to a system and method for using slightly diverging orthovoltage x-ray minibeams (referred to herein as "OXM"), which are formed by a multi-aperture collimator positioned on the surface of a subject's skin, to form an effective beam of therapeutic radiation at a predetermined tissue depth for treating a targeted tumor or other abnormality, while sparing the skin and a substantial portion of the tissue proximal to the target from radiation damage. The effective beam, which may be a substantially solid, or unsegmented beam, is formed by the merging of the x-ray minibeams. The method utilizes the slight divergence of the minibeams emerging from the multiple apertures, which is due primarily to the relatively large, finite, x-ray source spot size compared to the relatively small source-to-collimator distance. The depth at which the effective beam of therapeutic radiation is formed is adjusted by proper selection of source size, aperture size (which determines the size of each minibeam at the skin), and source-to-collimator distance.

An effective beam of therapeutic radiation refers to a beam having a dose profile (perpendicular to the x-ray beams) at a particular tissue depth across which the dose level required to have a therapeutic effect is maintained. The minibeams of the present disclosure merge sufficiently to form the effective beam of therapeutic radiation. If there are any discernible "valleys" in the profile as a result of forming the effective beam by merging of the minibeams, the valley dose in the effective beam of therapeutic radiation must still be high enough to correspond to a therapeutic radiation dose. An effective beam of therapeutic radiation having no measurable peak-valley "pattern," or having only a small modulation or peak-valley dose ratio (PVDR) of 1.10 (10% modulation) or less, is referred to herein as a "solid" beam of therapeutic radiation.

The term "collimator" is sometimes used interchangeably herein with "multi-aperture collimator" to refer to the multi-aperture collimator (which may be a multi-slit collimator) used to form the orthovoltage minibeams at the surface of the skin of a subject. The multi-aperture collimator should not be confused with a beam-shaping collimator, also known in the art as a "multi-leaf collimator," which may also be used to shape the orthovoltage x-ray beam of the present disclosure to conform to the overall shape of the target. The multi-leaf collimator is preferably positioned to shape the orthovoltage x-ray beam before the beam is segmented into minibeams by the multi-aperture collimator.

The term "target" used herein refers to the tissue that is targeted to receive a therapeutic dose of radiation. The target encompasses the tumor or other targeted abnormality, for example, an epileptic lesion or epileptogenic foci, and may also include an immediate margin of tissue surrounding the target tumor or abnormality. One of skill in the art will understand how to select the amount of surrounding tissue included in the target to insure that all tumor cells, for example, that may have spread to the immediate tissue surrounding of the tumor are exposed. For other abnormalities, the margin included in the volume defined by the target may be extremely small, and may be based primarily on the system's accuracy in targeting the volume of interest.

"Tissue depth" is generally used to indicate a subcutaneous depth.

"Proximal" is used herein to indicate a location downstream of the x-ray source and multi-aperture collimator, but upstream of the target, i.e., located on the side of the target closest to the x-ray source.

"Distal" is used herein to indicate a location downstream of the target, i.e., located on the side of the target away from the x-ray source.

The orthovoltage x-ray minibeams emerging from the multi-aperture collimator of the present disclosure are slightly diverging, largely due to the penumbra effect. This results from the relatively large focal spot size (e.g., 3 to 5 mm) of the orthovoltage x-ray source compared to the relatively small source-to-collimator distance (20 to 45 cm). The expected amount of divergence may be estimated through calculations, and is based upon the x-ray source size (for example, the focal spot size formed on the anode of an orthovoltage x-ray tube) and the distance between the x-ray source (focal spot) and multi-aperture collimator.

Using the geometric estimates of the divergence of the minibeams, other parameters of the system, as described further herein, can be varied to deliver an effective beam of therapeutic radiation to the target by sufficient merging of adjacent minibeams. In preferred embodiments, parameters are optimized such that the minibeams merge sufficiently to form a solid, or substantially solid, effective beam of therapeutic radiation proximal to the edge of the target.

As one of skill in the art will appreciate, while the tissue depth at which the minibeams will merge sufficiently to provide an effective beam, which may, in embodiments, be a solid beam, of therapeutic radiation can be calculated, phantom targets such as water, or chromographic film, are also preferably used to calibrate and tweak the system before administering any treatment.

Figure 2A:
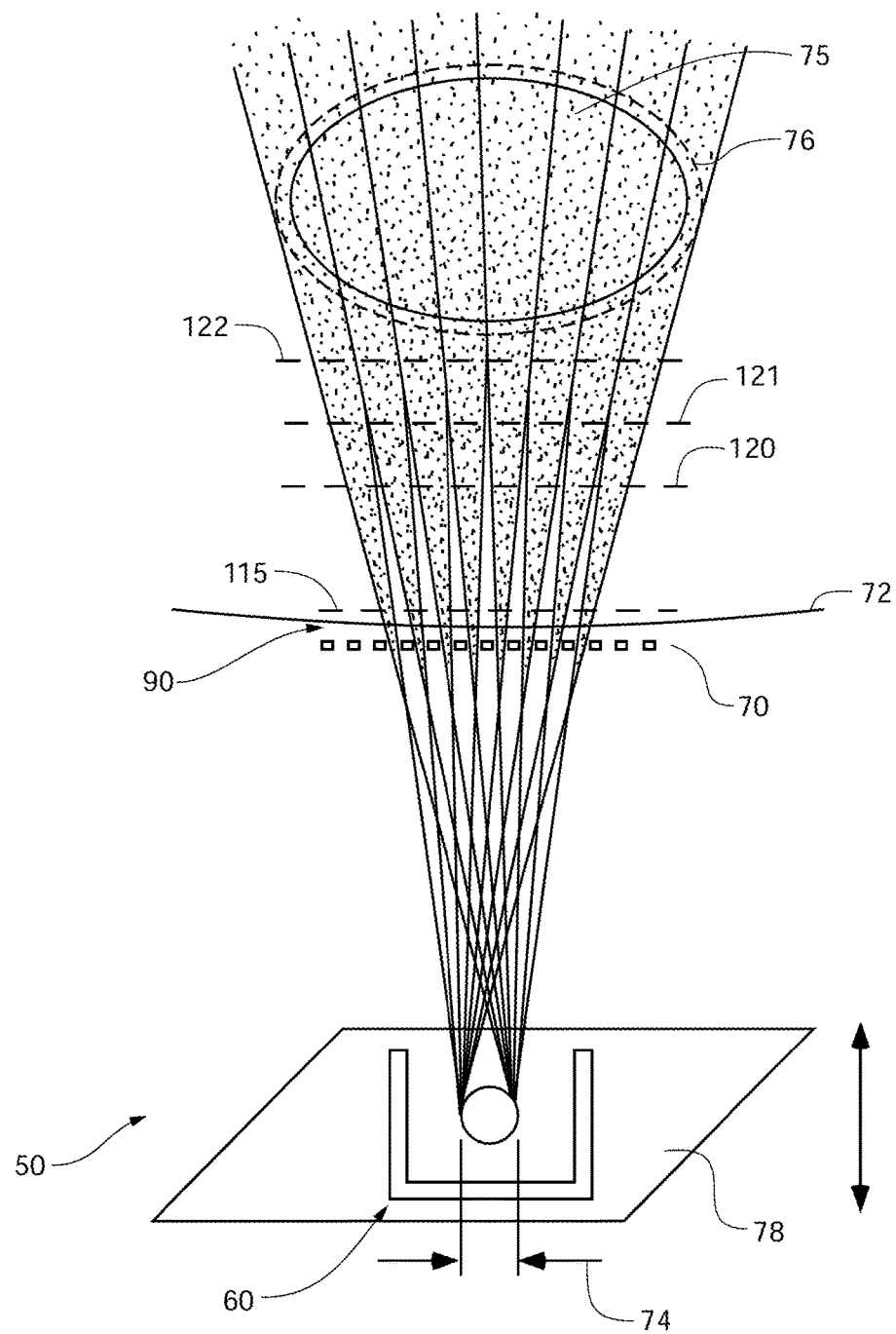
FIG. 2A is a pictorial representation of an embodiment of a system for practicing a method of the present disclosure.
Figure 2C:
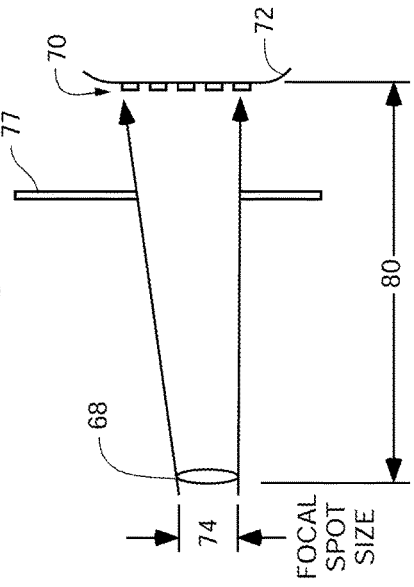
FIG. 2C is a pictorial representation of a portion of an embodiment of a system for forming a minibeam array of orthovoltage x-rays of the present disclosure.
Figure 2D:
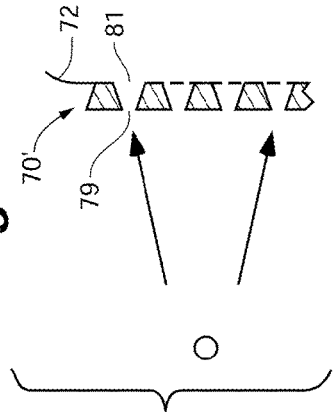
FIG. 2D is a pictorial representation of a plate multi-aperture collimator of the present disclosure.
Figure 2B:
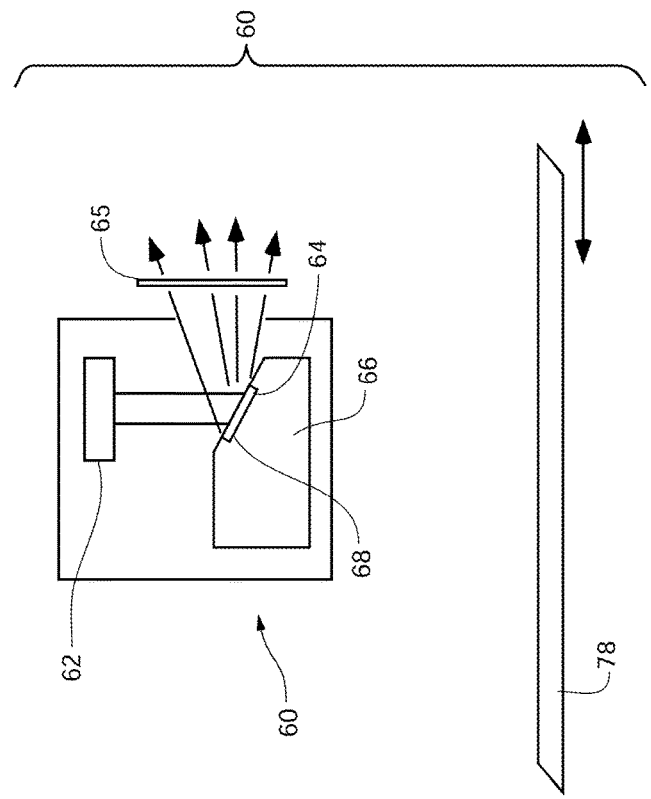
FIG. 2B is a pictorial representation of an embodiment of an orthovoltage x-ray device of the present disclosure.

Referring to FIG. 2A through 2C, an embodiment of a system 50 for implementing the methods of the present disclosure for delivering an effective beam of therapeutic orthovoltage x-ray radiation to a target 76 includes an orthovoltage x-ray tube 60 and a multi-aperture collimator 70 for placing in close proximity to, or in preferred embodiments, on the surface of, the skin 72 of a patient. In embodiments, a multi-leaf collimator 77 is also positioned between the x-ray tube 60 and the multi-aperture collimator 70 for shaping the beam emerging from the tube 60 to conform to the overall shape of the target. Referring to FIG. 2A, the multi-aperture collimator 70, which is aligned within the trajectory of the x-ray beam, may be touching the patient's skin, and slightly pushing against the skin 72.

For targets in the chest and the abdomen that move extensively with the breathing motion, pushing the multi-aperture collimator hard against the skin completely immobilizes the skin and advantageously creates pressure that helps immobilize the tissue to limit possible beam smearing with the tissue movement, particularly for tissue within the critical first centimeter and possibly further from the skin. The smearing of the dose pattern of minibeams at deeper tissue depths will not be as critical, since the minibeams will be broadening and typically beginning to merge within a few centimeters of tissue depth.

In embodiments, any blurring of the minibeam array dose pattern because of the breathing movement of the patient's body can be minimized by aligning the direction of the incident minibeams so that the beams are perpendicular to the surface of the body being treated, or parallel to the lines of displacement of the body tissues being treated, within up to ±15°.

Referring still to FIG. 2A, the target 76 encompasses a tumor 75 or other targeted abnormality, for example, an epileptic lesion or epileptogenic foci, and also includes an immediate margin of tissue surrounding the target tumor or abnormality. In tumor therapy, typically a 5-mm margin is set around the tumor. One of skill in the art will appreciate that the margin is selected to cover for the uncertainties involved in radiation therapy to insure that the entire tumor is treated at the full dose. Such uncertainties come from, inter alia, tumor imaging, tumor positioning in the beam, dosimetric calculation, and the diffuse edge of the tumor.

Referring to FIG. 2B, the orthovoltage x-ray tube 60 may be constructed by any suitable means in the art. In embodiments, the tube 60 includes a cathode 62, which expels and focuses electrons onto the surface 64 of an anode 66 formed of an appropriate target material, such as tungsten. The x-ray source 68 for generating the orthovoltage x-rays in this embodiment is a focal "spot" 68 (which can be also be in the form of a line depending on the construction of the tube 60) formed on the anode surface 64. Referring to FIG. 2C, as well as FIG. 2A, the x-ray source, or focal spot 68, is characterized by an x-ray source (focal spot) size 74 defining an area that emits orthovoltage x-rays.

In embodiments, the system 50 also includes beam hardening filters 65 appropriately positioned in the path of the x-ray beam generated by the anode.

In embodiments, the orthovoltage tubes of the present disclosure are between about 100 kVp and 500 kVp. In particular embodiments of the system and method of the present disclosure, the x-rays are produced by orthovoltage tubes of higher kVp, for example, between about 250 kVp to about 500 kVp, and preferably, between about 300 kVp and about 500 kVp.

In additional embodiments, the x-ray tubes of the present disclosure may have up to 30 mA current, and preferably at least 25 mA current.

The beam hardening filters in embodiments are copper filters of one to several millimeters of thickness, selected to preferably eliminate most of the low-energy end of the spectrum. As a result, hard and penetrating beams such as with ~4 cm or larger tissue HVL are produced. Such beam energies are adequate to treat many types of tumors located at different depths, including those of the breast, the head-and-neck, the brain, and certain tumors of the chest and abdomen.

Referring still to FIG. 2A and FIG. 2B, the system 50 may also include a translation apparatus 78 for changing a source to collimator distance 80 between the location of the focal spot 68 and the multi-aperture collimator 70. While the translation apparatus 78 as shown can translate the x-ray tube 60 closer to, or further from the patient, in other embodiments, the translation apparatus may instead be associated with the device or gantry on which the patient is positioned. Additional degrees of freedom are also preferably provided on the gantry (not shown), and/or on the system, for correctly positioning the patient so that the target 76 is accurately positioned within the trajectory of radiation produced by the x-ray tube.

The x-ray tube, multi-aperture collimator, and patient are positioned such that the target 76 is within the trajectory of the orthovoltage x-rays emitted from the focal spot 68. Spatially distinct, and slightly diverging x-ray minibeams 90 are formed on the surface of the skin as a result of the orthovoltage x-rays impinging on the multi-aperture collimator 70.

Referring to FIG. 2D, to accommodate the thickness of the multi-aperture (including multi-slit) collimators of the disclosure, and the divergence of the minibeams, in embodiments, the collimator 70' as shown in FIG. 2D may be flared, such that an output width 81 is sufficiently larger than the input width 79 of each aperture or slit to avoid any interference of the minibeam with the walls of the collimator.

Figure 3A:
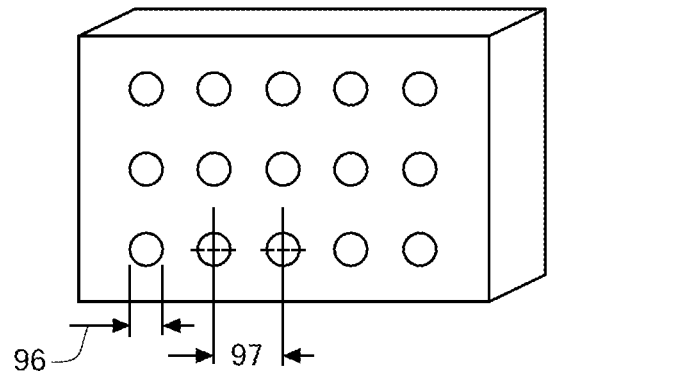
FIG. 3A is a pictorial representation of an embodiment of a multi-aperture collimator of the present disclosure.

In embodiments, the multi-aperture collimator 70 may be a multi-aperture plate 92 with round apertures, such as that shown in FIG. 3A, which may be flared like the collimator 70' shown in FIG. 2D, and which segments the x-ray beam into a minibeam array 90 of nearly parallel, slightly diverging pencil-like beams. In other embodiments, the collimator 70 is a multi-slit collimator 94, such as that shown in FIG. 3B, which may also be flared like the collimator 70' shown in FIG. 2D, and which segments the x-ray beam into a minibeam array 90 of slightly diverging planar beams. The minibeams are of sub-millimeter width, e.g., diameter 96 (pencil beams) or thickness 98 (planar beams), and are separated by a center-to-center spacing 97.

The multi-aperture collimators of the present disclosure may be heavy-metal collimators, comprised of a material such as tungsten. In embodiments, the heavy-metal collimators have a thickness of between about 5 to about 20 mm. Such relatively thin multi-aperture collimators for use with orthovoltage x-rays in accordance with the present disclosure can be made, for example, of a plurality of thin tungsten-alloy blades with spacers between them, held by a rigid frame. In other embodiments, the tungsten multi-aperture collimator can be made of wire cuts in a tungsten alloy plate.

In embodiments, an array of pencil beams may be configured to conform to the shape of the source spot size on the anode, even without a beam-shaping, or multi-leaf, collimator. In embodiments, the dose distribution produced by the array of pencil minibeams penetrating the subject as a function of depth in tissue will have a nearly cylindrical uniformity.

In embodiments, pencil beams may have a cross-section that is round, like those formed by the multi-aperture collimator of FIG. 3A. In other embodiments, the pencil beams may be formed by multi-aperture collimators having elliptical, square, rectangular, or polygonal apertures, or configured in any other useful shape for forming the arrays.

It is noted that while planar beams may provide a less uniform dose distribution, they can provide a larger yield of beam throughput, particularly for oval or elongate-shaped focal spots.

In embodiments, for planar, e.g., narrow and elongated, minibeams, the shape of the focal spot 68 is oval or elongated. This allows conformity between the shape of the incident beams and the pattern of planar minibeams to be produced. In further embodiments, the collimator has a pattern of planar slits, such as those in FIG. 3B, and they are aligned with the direction of the elongated length of the spot size. This combination will produce both a high throughput of the beam through the multi-aperture collimator and a uniformity of dose distribution produced by the minibeams as a function of the depth in the tissue.

In the system and method of orthovoltage x-ray radiation therapy of the present disclosure, each of the minibeams in the spatially distinct array of minibeams produced by the multi-aperture collimator 70 at the skin preferably has the same width and center-to-center spacing. The width (e.g., diameter or thickness) of each of the minibeams preferably has a value chosen between about 0.1 mm and about 0.6 mm, preferably, about 0.3 mm.

The minibeams are spaced regularly and closely together by a center-to-center distance, which may be chosen, for example, from a value ranging between about 0.1 and about 1.0 mm inclusive, depending on the minibeam width, depth of the target and other factors described further herein.

In embodiments, the center-to-center distance between adjacent minibeams may be a value ranging between about 0.5 mm and about 1.6 mm, depending on the minibeam width, depth of the target and other factors described further herein.

This submillimeter size of the segmented minibeams within the non-target tissue (proximal to the target) results in a very large tissue-sparing effect, that, while recognized for synchrotron x-ray therapy using parallel (non-diverging) minibeam arrays, as described, for example, in U.S. Pat. No. 7,158,607 to Dilmanian, et al., is not known in the prior art of orthovoltage x-ray systems for radiation therapy.

As described herein, the orthovoltage x-ray tubes of the present disclosure operate at voltages of up to 500 kVp, preferably between about 300 kVp and about 500 kVp. This higher voltage advantageously allows the x-ray beams to be significantly filtered, with up to several mm of copper, e.g., to attenuate the low-energy end of the spectrum. This in turn increases the median energy, i.e., hardens the beam, resulting in a significant increase in the depth of dose penetration to the tissue of up to 8 cm or more tissue HVL.

Due to these characteristics of the x-ray tube of the present disclosure, in combination with the multi-aperture collimator construction and geometry, the minibeams in the arrays generated in accordance with the present disclosure can stay very narrow for many centimeters inside the subject. By further adjusting the geometry of the beam administration, the tissue depth at which the minibeams merge is very well-controlled in accordance with the present disclosure to allow administration of an effective beam, which may be, in embodiments, a solid beam, of therapeutic radiation to the target, while avoiding damage to both the skin and the tissue proximal to the target.

Additional features and embodiments of the system of the present disclosure are described and understood in the details of the methods further described herein. Furthermore, it is understood that any details of embodiments of the disclosure described as elements of the system may also be embodied in methods of the present disclosure.

Referring to FIG. 4A, an embodiment of a method 100 of the present disclosure for delivering therapeutic radiation to a target within a subject, while sparing the skin and, preferably, substantial portions of tissue proximal to the target from radiation damage, includes positioning, at 102, a multi-aperture collimator, such as a heavy-metal collimator plate, on the surface of the skin within a trajectory of radiation produced by an orthovoltage x-ray tube. The target is located at a known, predetermined depth as measured from the irradiated portion of a surface of the skin of the subject. The multi-aperture collimator is configured to generate an array of slightly diverging, spatially distinct, minibeams. In embodiments, the minibeams have a predetermined center-center spacing, which may be from about 0.1 mm to about 1.0 mm inclusive, and a width of between about 0.1 mm and about 0.6 mm inclusive. At 104, the skin is irradiated with the array of orthovoltage x-ray minibeams emerging from the multi-aperture collimator. The method 100 further includes, at 106, delivering an effective beam, which may be, in embodiments, a solid beam, of therapeutic radiation to the target. The effective beam is delivered by, at 108, controlling a tissue depth from the irradiated surface of the skin at which adjacent orthovoltage x-ray minibeams in the array sufficiently merge to form the effective beam, and while sparing, at 116, at least a substantial portion of tissue proximal to the target. The sparing of tissue may be further enhanced by limiting the width of the minibeams in the proximal tissue, at 118, before they merge to form the effective beam of therapeutic radiation, to 1.0 mm or less. In other embodiments, the width of the minibeams before they merge to form the effective beam of therapeutic radiation is limited to 0.7 mm or less.

In embodiments, a depth of the tissue sparing in the body can be varied anywhere from about 1 cm, when the front edge of the tumor is close to the surface, to 40 cm in embodiments in which the tumor is deeper.

Figure 4B:
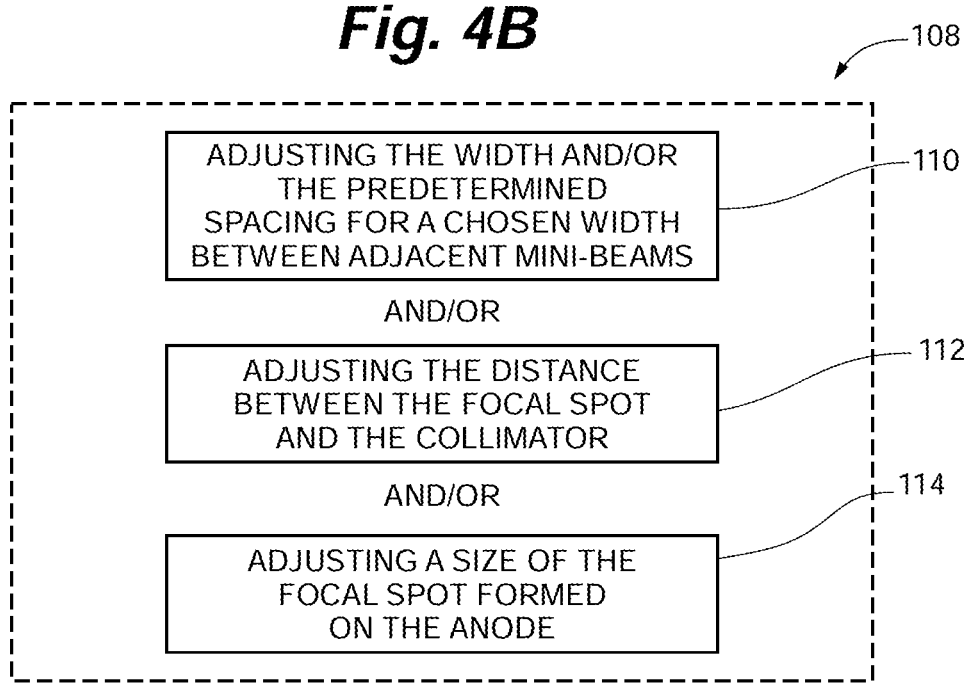
FIG. 4B is a block diagram representation of additional embodiments of a method of the present embodiment.

Referring to FIG. 4B and FIG. 2B, for example, as described further herein, in embodiments of the system and method of the present disclosure, the tissue depth at which the adjacent minibeams merge sufficiently to form the effective beam is controlled by adjusting one or more parameters of the system. For example, any one or combination of adjustments listed in FIG. 4B may be used to control the tissue depth at which the minibeams merge to form the effective beam. For example, at least one of the predetermined spacing 97 and the width 96, 98, between adjacent minibeams may be adjusted, at 110, and/or a distance 80 between the focal spot 68 and the multi-aperture collimator 70 may be adjusted, at 112. In embodiments, controlling the tissue depth at which the adjacent minibeams merge to form the effective beam may further, or alternatively, include, at 114, adjusting a size of the focal spot 68 formed on the anode.

Referring again to FIG. 2A, the small divergence angle of each of the minibeams in the array 90 results from the penumbra effect of a relatively large source spot size 74, which, in embodiments, may be between about 3-5 mm, positioned a relatively short distance away from the multi-aperture collimator 70. In embodiments, the distance between the focal spot 68 and collimator 70 may be between about 5 and about 20 cm.

In embodiments, magnitudes of the divergence angle of the individual minibeams of the present disclosure are about +/−10 milliradians, i.e., the minibeams form cones having a full divergence angle of about 20 milliradians.

In reference to FIG. 2A and FIGS. 5A-5D, the minibeams gradually merge as they travel further away from the skin towards the target, i.e., to deeper tissue depths. Referring to the simplified pictorial representation of the diverging beams shown in FIG. 2A, a geometric calculation can be made to estimate the parameters for obtaining a solid beam, for example, at a known tissue depth, by merging of the minibeams. The calculations are based on the divergence angle of the minibeams as further described herein. The actual dose profiles resulting from the increasing overlapping of the minibeams as they penetrate the tissue are best shown, however, in actual stepwise cross-section profiles measured as a function of depth, as shown in FIGS. 5A to 5D.

The dose profiles of FIGS. 5A to 5D were produced using a 320-kVp orthovoltage x-ray generator with a source size of about 4 mm, a source-to-collimator distance of about 260 mm and with a multi-slit collimator configured to produce 0.3-mm minibeams with 0.7-mm beam spacing on-center.

FIG. 5A represents the dose profile of the minibeams exiting the multi-slit collimator (tissue depth of 0 mm). FIGS. 5B through 5D were measured at distances of 13, 27, and 40 mm, respectively, from the multi-slit collimator. As described further below, the minibeams gradually lose their tissue sparing effect at increasing depths, or increasing distances from the multi-slit collimator, as the gaps between them decrease, while the therapeutic efficacy across the merging minibeams' dose profile increases as the dose between the minibeams (the "valley dose") increases. The minibeams completely merge at about 40 mm, as shown in FIG. 5D.

As shown in FIG. 5A, the shape of the individual minibeams just emerging from the multi-slit collimator are already somewhat bell-shaped because of the source and collimator geometries involved. As these individual minibeams broaden with depth, the tails of the dose profiles start partially overlapping with their neighbors, producing a segmented pattern of "peaks and valleys" of neighboring minibeams. The continuation of beam broadening gradually increases this partial overlap, resulting in an increase in the height of the valley and an increasingly more uniform-looking pattern. The peak-to-valley dose ratio (PVDR) decreases at increasing depths as the adjacent minibeams merge. The PVDR of adjacent minibeams for each of the depths 0 mm, 13 mm, 27 mm, and 40 mm in FIGS. 5A-5D is about 5.9, 3.1, 1.3 and 1.03, respectively. At the depth of 40 mm, as shown in FIG. 5D, the PVDR of adjacent minibeams is essentially unity (1.03) and the profile resembles that of a unitary, conventionally-formed, beam. The beam profile no longer appears segmented or modulated, but instead represents a solid beam profile. Therefore, for this example, a solid effective beam of therapeutic radiation can be formed at least by the time it reaches a depth of 40 mm. In embodiments of the present disclosure, a solid effective beam of therapeutic radiation is formed from the merging minibeams proximal to the edge of the target, such as a tumor.

The following calculates the depth in the tissue at which the minibeams would be expected to merge to form a solid, unsegmented beam in a hypothetical simplified geometry used to clarify the basic concept of beam broadening due to the opening angle of each minibeam, based on the parameters used to generate the plots shown in FIGS. 5A to 5D. Neglecting the 0.3-mm width of the collimator slit, the opening angle of the minibeams coming out of the multi-slit collimator will be about 0.0154 radian (4/260), that is 15.4 milliradian. Furthermore, neglecting the 4-mm source size and the minibeam broadening effects produced by the un-sharp edges of the source and collimator, the minibeams broaden to a sharp 0.70 mm at a distance of about 45.4 mm from the multi-slit collimator (0.0154 radian×45.4 mm=0.70 mm). This means that the sharp edges of the adjacent minibeams touch each other at about 45.4 mm from the multi-slit collimator to produce a solid beam.

The inaccuracies introduced in these calculations by neglecting the finite size of the collimator slit slightly affect a) the opening angle of the minibeams, and b) for a given opening angle, the actual broadening of the beam. These two factors can be corrected for by convoluting the calculations both angularly and laterally with the widths of the collimator's opening. The corrections not only will slightly add to the actual width of the minibeams at any given distance from the multi-aperture collimator but also un-sharpen the edges of the minibeams as they pass through the tissues. Furthermore, the inaccuracies introduced by neglecting the actual rounded shape of the source spot size, rounded edges of the collimator, and by scattering of the x-rays in the subject, will also lead to slightly wider beams and slightly more roundedness of their edges.

All these effects give the incident minibeams their "bell-shaped" feature with extended "tails," as seen in FIGS. 5A-5D, instead of a sharp "rectangular" shape. As a result, the beam-merging event results as a gradual overlapping of the dose profiles (perpendicular to the x-ray beams) of the adjacent minibeams with each other as shown in FIGS. 5A-5D. This also means that the merging of the minibeams is a gradual process in which the "valley" doses gradually rise and the "peak" doses gradually decline as neighboring peaks and valleys eventually reach substantially the same height (ignoring non-uniformities due to other causes), thus eventually producing a uniform, unsegmented, beam with a PVDR that is substantially equal to unity across the beam profile.

In embodiments of the method and system of the present disclosure, an effective beam of therapeutic radiation for delivery to the target is formed by merging the minibeams sufficiently to form a dose pattern (perpendicular to the x-ray beams) wherein any residual "valleys" are still high enough to correspond to a therapeutic radiation dose. Accordingly, the minimum (valley) dose in the dose pattern (perpendicular to the x-ray beams) of the beam due to the merging of the minibeams will be equal to or greater than the minimum effective therapeutic dose, so that an effective therapeutic dose of radiation is delivered across the entire dose pattern formed by the merging minibeams and across the corresponding target area.

In embodiments, the effective beam of therapeutic radiation formed by merging of the minibeams at a particular tissue depth has a substantially unsegmented dose pattern that has no detectable modulation or that is characterized by a PVDR (of neighboring minibeams) that is close to unity and can thus be referred to as a solid beam of therapeutic radiation. It is understood that while the PVDR may be unity, or approximately unity, the overall beam profile across the target will generally not be uniform due to the shape of the source beam, as shown, for example, in FIG. 5D, which shows a slight gradual increase in the profile from left to right.

In other embodiments, depending on the geometry and sharpness of the edges of the multi-aperture collimator, the effective beam formed from the merging minibeams may have an inherent heterogeneity of dose deposited in the tumor in the areas where adjacent minibeams merge, which have an additive affect (not related to the PVDR) and can provide streaks of amplified dose that generate a concomitant boost within the tumor.

In embodiments, the PVDR in the dose pattern of the effective beam of therapeutic radiation delivered to the target is no greater than 1.5.

In embodiments, the PVDR of the effective beam of therapeutic radiation delivered to the target is no greater than about 1.3.

In additional embodiments, the PVDR of the effective beam of therapeutic radiation delivered to the target is no greater than about 1.2.

In embodiments, the effective beam of therapeutic radiation delivered to the target is essentially a solid beam, having less than 1.10 PVDR, or having no detectable PVDR or modulation corresponding to the array of minibeams that merged to form the solid beam.

Referring again to FIG. 2A, FIGS. 5A-5D provide examples of the actual beam dose profiles as the minibeams merge. In FIG. 5A, the dose profile 124 was generated at a simulated tissue depth 115 just after the multi-aperture collimator. FIG. 5B shows the dose profile 126 at a depth 120 of 13 mm, at which the tails of the minibeams have begun to merge. At a further depth 121 of 27 mm, shown in FIG. 5C, a lower PVDR 135 of about 1.3 to 1 is evident as the valley dose rises and the resultant beam profile begins to lose its segmented appearance. At a tissue depth 122 of 40 mm, the beam profile 130 is no longer modulated or appears segmented (PVDR approaches unity or is undetectable—in this case, PVDR is estimated to be about 1.03) at least across most of the beam profile such that the adjacent minibeams have merged to form a solid beam of therapeutic radiation.

Referring to FIGS. 6A-6C and FIG. 4B, the system and method of the present disclosure include controlling the tissue depths at which the minibeams merge such that an effective beam, which may be a solid beam, of therapeutic radiation is delivered to the target, while sparing the skin and as much of the proximal tissue as possible. Any one or more of a number of parameters may be varied to achieve this desired result, such as: adjusting the spacing and/or width of the apertures in the collimator; adjusting the focal spot to collimator distance; adjusting a focal spot size of the anode. FIGS. 6A-6C illustrate the result of varying just the source-to-collimator distance for a particular anode and multi-aperture collimator. The source to collimator distance 140 in FIG. 6B allows an effective beam of therapeutic radiation to be delivered to a tumor 143 at a predetermined tissue depth 142. Referring to FIG. 6A, increasing the source-to-collimator distance 144, allows a deeper tumor 145 to be treated with an effective beam of therapeutic radiation at a deeper predetermined tissue depth 146. Similarly, referring to FIG. 6C, decreasing the source-to-collimator distance 148, allows a shallower tumor 147 to be treated with an effective beam of therapeutic radiation at a deeper predetermined tissue depth 146. As demonstrated, the shorter source-to-collimator distance increases the divergence of the individual minibeams, thus making them merge with each other at a shorter tissue depth.

Figure 7A:
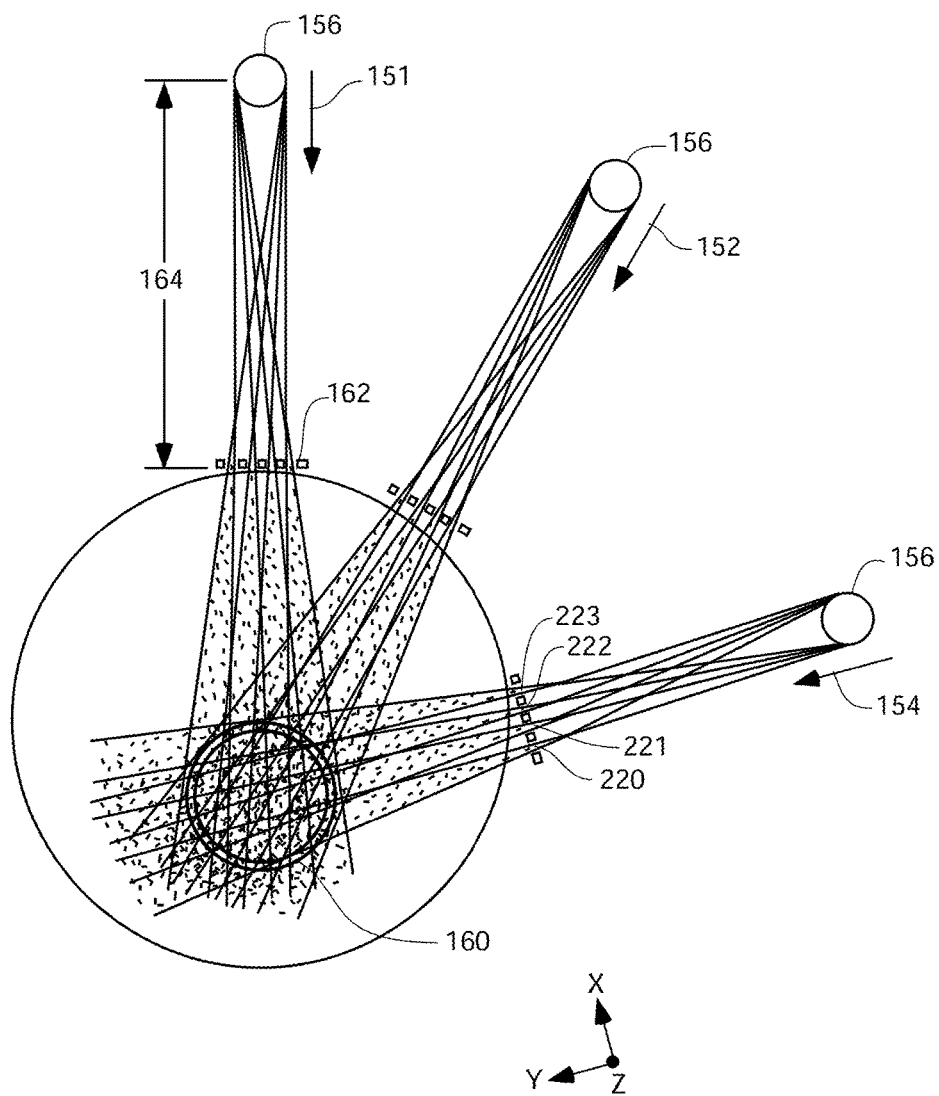
FIG. 7A is a pictorial representation of the implementation of the system of FIG. 2A in accordance with another embodiment of a method of the present disclosure.

Referring to FIG. 7A, in embodiments of the method of the present disclosure, treatment planning for a patient includes repeating the method described above and in FIGS. 4A and 4B for additional exposure directions or trajectories after the first exposure from trajectory 151. It will be appreciated that the radiation formalism may be adjusted for each of the trajectories 151, 152, 154 from a focal spot 156 of an orthovoltage x-ray tube, to make effective beams of therapeutic radiation, which may be solid beams, at the proximal side of the target 160, by adjusting either the center-to-center spacing of apertures in the multi-aperture collimator 162 for the subsequent exposures 152, 154, or the distance 164 between the source 156 and the collimator 162, or by adjusting the spot size from the focal spot 156.

FIG. 7A shows minibeam administrations from three shallow angles aimed at a tumor and its margin. As shown, the merging point of the minibeams at which an effective beam is formed does not necessarily have to occur immediately before or at the edge of the target as long as it does not produce much proximal tissue burden. As discussed herein supra, an effective beam of therapeutic dose may be produced slightly before the geometrically calculated merging point for forming a solid beam due to, inter alia, radiation leakage between the minibeams.

One will appreciate that the target will generally not be formed into any symmetrical volume. The outer shape of the target onto which the x-ray radiation is projected, as well as the thickness profile of the target to be treated, will change based on the direction from which it is irradiated. A beam-shaping collimator, such as a multi-leaf collimator, is preferably positioned between the x-ray source and the multi-aperture collimator and adjusted to conform to the shape of the target as projected on a plane perpendicular to the trajectory of x-rays. In embodiments, the multi-aperture collimator can be continuously adjusted, preferably being automatically and dynamically controlled using computer processors and controllers, as the direction of irradiation of the target changes in accordance with any of the methods of the present disclosure.

It is also noted that adjacent arrays can collide without producing "star dose pattern," i.e., a region of mixed-angle minibeams, if the collision occurs after the merging points of the arrays.

One of skill in the art will appreciate that the multiple exposures from different directions may be administered during a single treatment session, or in different treatment sessions.

Figure 7C:
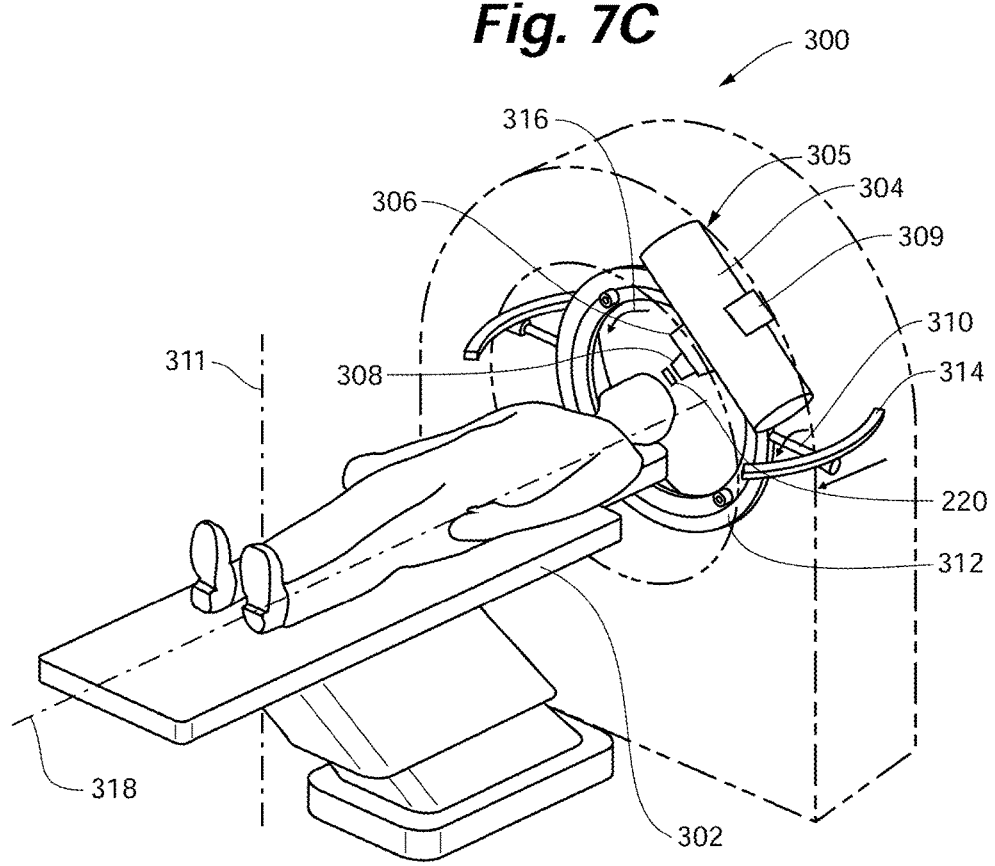
FIG. 7C is a pictorial representation of a gantry for positioning the system around a platform on which a subject is positioned for treatment.

Referring to FIGS. 7A-7C, embodiments of the system of the present disclosure may include a gantry 300, as known in the prior art, to align the trajectory of radiation onto the target. The subject being treated is positioned on a platform 302, or bed, which may have at least translational alignment capabilities for positioning the subject in the aperture of the gantry 300 and aligning the target within the trajectory. In embodiments of the system of the present disclosure, the x-ray source 304, beam-shaping collimator 306, and multi-aperture collimator 308 are preferably mounted together as a unit 305 (the unit 305 also having positioning elements as described in reference to FIGS. 2A-2C for controlling the tissue depth at which the minibeams merge). The multi-aperture collimator and beam-shaping collimator remain aligned on unit 305 within the trajectory of orthovoltage x-rays emitted from the x-ray source 304, as the unit 305 is rotated and/or translated relative to the target. Rotational and translational arms or mounting platforms are provided on the gantry, on which the unit 305 is operatively positioned, to allow the trajectory of the x-rays to be positioned on the target and to allow the direction from which the target is irradiated to be changed in a step-wise, as well as in a continuous fashion, to perform the methods described herein.

The gantry 300 may, for example, include a tilt axis 310 and a rotatable ring 312 on which the unit 305 is mounted. The unit 305 may be mounted to a radial translation stage 309 provided on the rotatable ring 312 for positioning the unit 305 radially toward or away from the center of the ring 312 so that the multi-aperture collimator 308 can be positioned on or near the subject's skin during treatment. Referring to FIG. 7A and FIG. 7C, the rotatable ring 312 may be tilted, for example, from its nominal vertical 311 or perpendicular plane relative to the horizontal platform 302 forward or back around the axis 310, and translated via a translational stage 314 as needed (alternatively, the platform 302 may be translated) to maintain the target within the trajectory of the beam, for any angular position, such as for trajectories 151, 152, 154 of FIG. 7A.

Figure 3B:
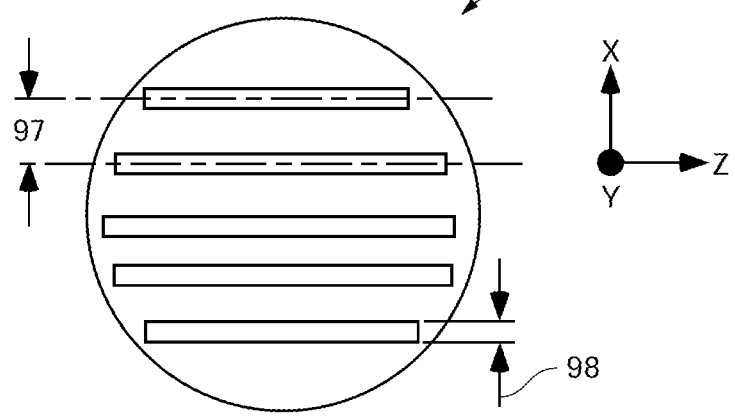
FIG. 3B is a pictorial representation of another embodiment of a multi-aperture collimator of the present disclosure for forming planar minibeams, which is referred to as a multi-slit collimator.

In embodiments, the multi-aperture collimator 162 of FIG. 7A is a multi-slit collimator. The multi-slit collimator 162 forms elongated planar minibeams, like those shown in FIG. 3B. In FIG. 3B, a cross-section of an array of minibeams perpendicular to the trajectory of x-rays (the trajectory extending into the plane of the paper of FIG. 3B, along a y-axis) is shown, where the elongated length of the minibeams, for example, minibeams 220, 221, 222, and 223 extends along the z-axis of the coordinate system of the array. For reference, the coordinate system for the same array of planar minibeams is shown in FIG. 7A for the trajectory 154. In FIG. 7A, the elongated length of the planar minibeams 220, 221, 222, and 223, and the slits or blades of the multislit collimator that generates them, extend perpendicular to the plane of the paper in FIG. 7A, along the z-axis.

Referring to FIGS. 7A-7B, for each of the three exposures of FIG. 7A, the array of planar minibeams can also be moved around the target on a continuous arc scan, the direction of the arc scan being shown in FIG. 7B, within planes perpendicular to the x-y plane of the cross-section of the array of slits shown in FIG. 7A (parallel to the slits of the collimator). Referring to FIG. 7C, the arcs of radiation may be formed by rotation of the x-ray source 304 with multi-aperture collimator 308 and preferably also beam-shaping collimator 306 aligned thereto (e.g., unit 305) along a direction 316 of the rotatable ring 312 to allow arc-scan of a brain tumor, for example, from different angles. The target is positioned at the center of the arcs.

The arcs merge to form an effective beam of therapeutic radiation at the same depth as would a single minibeam in the array, so that the effective beam, which may be a solid beam, of therapeutic radiation to the target is formed from merging of the adjacent arcs of radiation at the desired tissue depth. In additional embodiments, the arc is generated in a continuous step. Referring also to FIGS. 7A and 7B, for example, the arcs 230 can be generated at each of a plurality of positions 232, 234, 236 corresponding to trajectories and directions 151, 152, 154 for generating the minibeam arrays. Treatment can be implemented in one or more continuous arc motions of the source in planes parallel to a multi-slit collimator's blades, for example.

For reference, the orientation of the cross-section of one of the elongated planar minibeams 220 upon exiting the multi-slit collimator 308 is also shown in FIG. 7C. The direction of the arc scan 230 keeps the arcs of radiation formed from the minibeams individually separated as they exit the multi-slit collimator 308, and allows the arcs of radiation formed from the minibeams to merge at the desired tissue depth. The tissue depth at which the arcs merge is preferably adjusted dynamically during the arc scan to be proximal to the target at all times. This can be accomplished, for example, by continuously and automatically adjusting the source to multi-slit collimator distance to produce the optimal beam-merging tissue-depths.

Intensity modulation (referred to in the prior art as Intensity Modulated Radiation Therapy of IMRT) can also be performed during the arc scanning by continuously and dynamically adjusting the beam-shaping collimator and thus modulating the beam intensity during the arc scanning to conform the irradiation pattern to a shape of the target based on the direction of the x-rays forming the arcs of radiation relative to the target. The continuous rotating and translating of the moving parts of the gantry, adjusting/positioning of the leaves of the beam-shaping collimator, and adjusting of the distance between the x-ray source and the multi-collimator during the arc-scanning can be accomplished using automated circuitry, processors, and controllers according to methods known in the art.

Figure 8C:
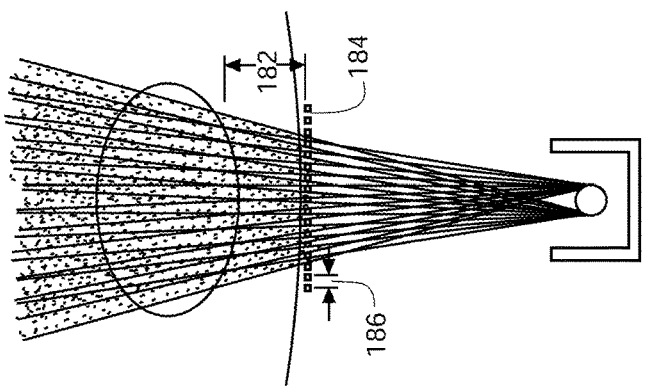
FIGS. 8A to 8C are pictorial representations of the implementation of the system of FIG. 2A to different target depths in accordance with yet another embodiment of a method of the present disclosure.
Figure 8B:
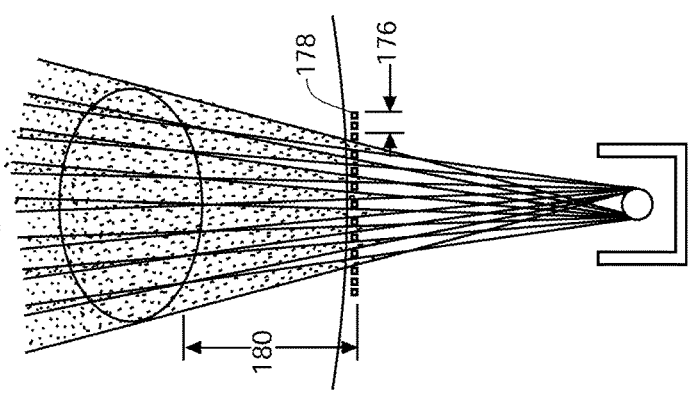
Figure 8A:
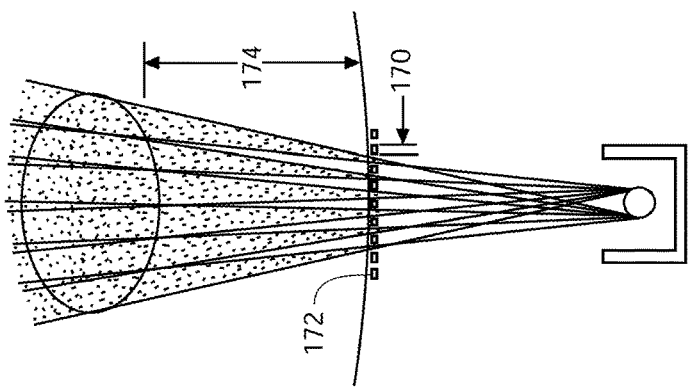

In embodiments, the multi-aperture collimator of the present disclosure, which is preferably a heavy-metal plate, is easily interchangeable. An embodiment of a system of the present disclosure may include pre-made multi-aperture collimators, each having different center-to-center spacing and a predetermined aperture size of, for example, about 0.3 mm. In embodiments, the set of collimators may include one or both of the pencil-beam type and planar-beam (multi-slit) type, of different widths and/or different center-to-center beam spacings. The appropriate multi-aperture collimator can then be used to change the depth at which the minibeams merge to produce an effective beam of therapeutic radiation as needed for the particular depth of the target, as shown in FIGS. 8A-8C, for example. A larger center-to-center spacing 170 between apertures in the collimator 172 of FIG. 8A is required to produce an effective beam, which may be a solid beam, of effective radiation at a deep target depth 174, than the spacing 176 of multi-aperture collimator 178 in FIG. 8B for the smaller target depth 180. Similarly, a shallower target depth 182 can be achieved using a multi-aperture collimator 184 in FIG. 8C with even closer center-to-center spacing 186.

Many advantages are realized using the system and method of the present disclosure over conventional MV x-ray radiation therapies. As shown in FIG. 9, for example, the beam energy spectrum 200 of a 320-kVp x-ray beam of the present disclosure can be heavily filtered to increase its median beam energy to about 220 keV mostly through the elimination of its low energy part. The resulting filtered beam 202 has a Cu half value layer (HVL) of 3.8 mm, which corresponds to a tissue HVL of about 10 cm. Comparing this 220 keV median beam energy with x-rays produced by MV electron linacs having an average median beam energy of about 1.5 MeV, the orthovoltage energy is about seven times smaller. This energy difference squarely puts the interaction with tissues of the orthovoltage beam in the photoelectric range, while that of the x-rays from MV linacs is in the Compton scattering range, with all their differential attributes as described above. The positive attributes of the 320-kVp x-rays of the present disclosure also include small dose fall-off at the target's edge, simplifying treatment planning.

FIG. 10 provides an example of the good dose penetration that is achieved with the present methods, allowing for targets essentially at any depth to be effectively treated with an effective beam, which may be a solid beam, of therapeutic radiation. FIG. 10 was constructed to show a relationship between orthovoltage x-rays' Cu half-value layer and a penetration depth in water for 50% dose penetration. The depth-dose curve 208 is plotted for a 300-kVp machine producing a spectrum with 2.45 mm Cu half-value layer. The curve's 50% dose occurs at a depth of 5 cm. Comparing this data with the spectrum of the orthovoltage x-rays of the present disclosure, as shown for example in FIG. 9, a relationship is detected between the beams' Cu half-value layer (HVL) and its 50% depth dose in water, indicating 5 cm water depth for 50% dose when using a spectrum with 2.45 mm Cu HVL, and 8 cm water depth for 50% dose with a spectrum of 3 mm Cu HVL. Accordingly, for 3.8 mm Cu HVL, the 50% dose penetration in water will occur at a depth of about 10 cm, which is considered to be a good dose penetration.

Figure 11:
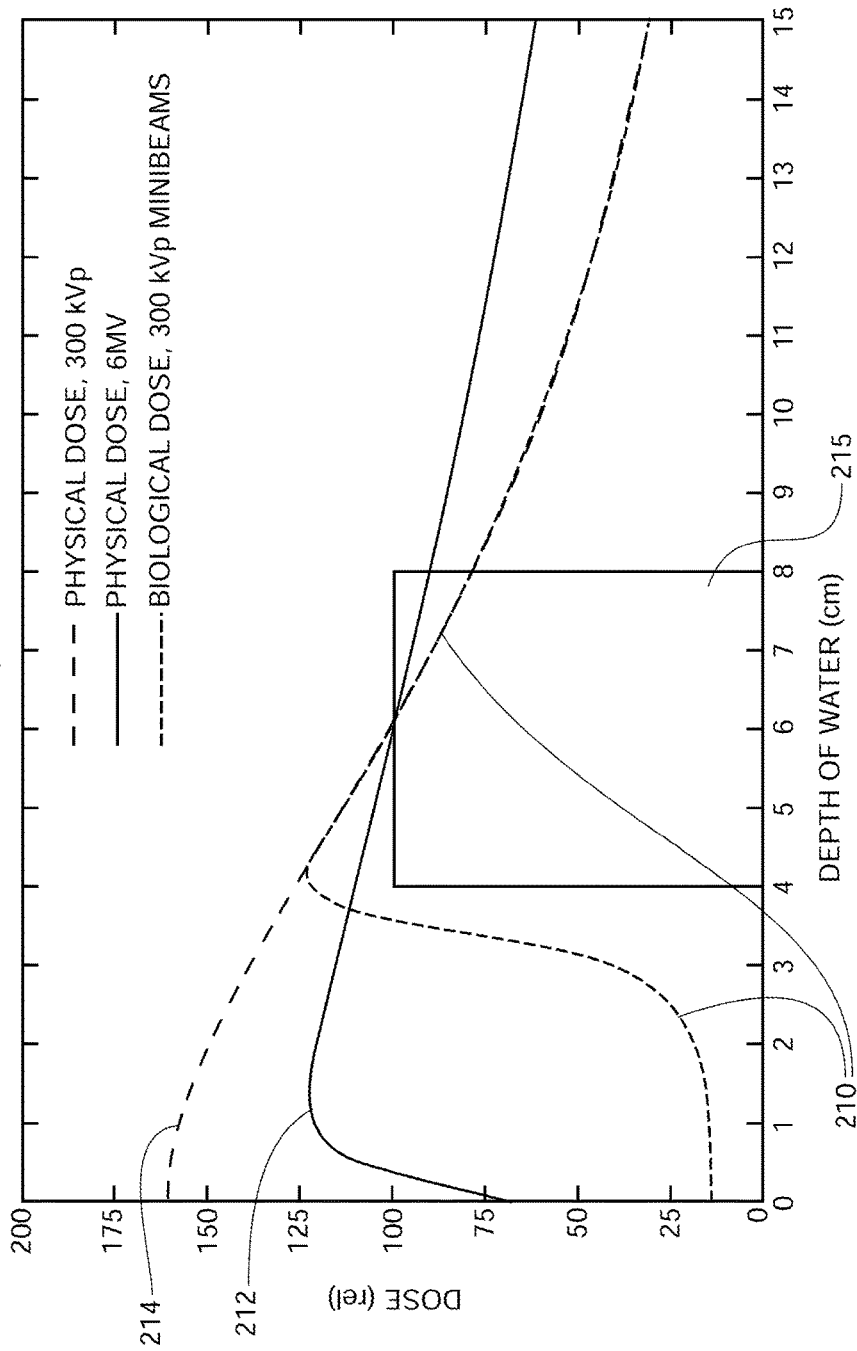
FIG. 11 is a graphical representation of the biologically effective dose as a function of tissue depth before and after the merging of orthovoltage x-ray minibeams to form an effective beam of therapeutic radiation in accordance with the present disclosure.

Another advantage of the present method is its application to deep tumors, for example, over 5 cm deep. Whereas conventional techniques for treatment of deep-seated tumors often depend on the target being positioned on the downward slope of the incident beam's depth dose curve, with the normal tissues positioned proximal to the target receiving greater dose than the target, using the system and methods of the present disclosure, the spacing between the minibeams can be adjusted so that the minibeams merge sufficiently with each other to produce an effective beam, which may be a solid beam, of therapeutic radiation near the proximal side of the target. This will spare a substantial portion of the normal tissue proximal to the target. FIG. 11 includes a plot drawn under the assumption that the minibeams begin to merge at about 5 cm depth. The lower curve 210 plots the biologically effective dose, which gradually increases in a transient region between about 3.5 cm to 5 cm in approaching the minibeams' merging point at about 5 cm, when the tissue-sparing effect is gradually diminished. Therefore the radiobiologically significant part of the curve 210 starts as one approaches 5-cm depth. This effect of sparing of the proximal tissues also ameliorates to a larger extent the problem of low tissue-depth penetration of the orthovoltage x rays.

FIG. 11 also illustrates the superior confinement of the dose of an effective solid beam produced by merging the orthovoltage x-ray minibeams of the present disclosure. The physical dose 214 produced by orthovoltage x-rays using a 300 kVp source with 3.8-mm Cu half-value layer (~8 cm water HVL) is plotted and compared to the biological dose 210, which is the effective tissue dose produced by an array of 0.3-mm minibeams spaced 0.7 mm on-center before they merge into a solid beam at ~5.2 cm tissue depth. Also for comparison, the physical dose 212 for 10 MV x-rays, which is the same as the biological dose for conventional MV x-ray, is plotted in FIG. 11. The physical 214 and biological orthovoltage dose 210 of the present disclosure and the dose 212 produced by the MV x-rays are super-imposed over the background 215 of a 4 cm target located 5 cm from the body's surface. As shown in FIG. 11, the biological dose 210 is much better confined to the tumor, both in the proximal and the distal sides, than the dose 212 produced by the MV x-rays.

Further, compared to the conventional radiation therapy methods using MV x-rays or also gamma rays, the present method produces smaller dose to the non-targeted tissues located distal to the target because of its lower beam energy and also produces smaller dose to tissues located lateral to the tumor or target than most conventional radiation techniques because of the smaller lateral penumbra of the orthovoltage x-ray beams.

To further enhance proximal tissue sparing, in embodiments, the width and predetermined center-to-center spacing of the minibeam array, and the distance between the focal spot and the multi-aperture collimator, are chosen such that each of the slightly diverging spatially distinct minibeams broaden to no more than 1.0 mm, or in other embodiments to no more than 0.7 mm, in width before they merge to form the solid beam.

The tissue-sparing effect of arrays of sub-millimeter parallel, thin planes of high-energy MeV synchrotron x-rays radiation, particularly when limited to 0.7 mm or less, was established in the early 1990s at the National Synchrotron Light Source (NSLS), Brookhaven National Laboratory (BNL). However, both the use and the tissue-sparing characteristics of sub-millimeter beams of orthovoltage x-rays in radiation therapy is heretofore unknown in the prior art. The enhanced tissue-sparing effect of minibeams of the present disclosure, when limited to 0.7 mm or less, is caused by two mechanisms, namely the "dose-volume effect" and the "prompt biological repair effect." The first effect, meaning that the smaller the target, the larger is its dose tolerance, has been known for many decades and its effect is not limited to millimeter or sub-millimeter beams. It has been the basis for such effects as grid therapy and stereotactic radiosurgery. The second effect, however, is indeed specific to beams with sub-millimeter dimensions and has been studied for high-energy synchrotron x-rays in recent years mostly in the context of animal studies, in the context of the repair of capillary blood vessels from sub-millimeter beam exposures. The effect has been shown for MV x-ray to be strongest for beams smaller or narrower than 0.7 mm. The inventors have advantageously discovered that a combined dose-volume and prompt biological repair effect is also realized for orthovoltage x-ray beams smaller or narrower than 0.7 mm of the present disclosure.

The methods of the present disclosure have particular advantages in certain clinical applications, such as for treating radioresistant tumors located near viable radiosensitive organs. In particular, radioresistant tumors of the head and neck are often not very large and are not located at large tissue depths, but they are often located near radiosensitive organs such as the parotid glands. For these applications, two attributes of the method are particularly helpful. First, the orthovoltage x-ray minibeams have a very sharp dose falloff, which significantly reduces the dose to the adjacent normal tissues. Second, due to the tissue-sparing of the method, tissues proximal to the target operate to spare such organs as the salivary glands, particularly the parotid gland. In fact, the minibeams can pass through the parotid gland on their way to the tumor located distal to them without damaging the gland, if the gland, which is positioned adjacent to the skin, is adequately thin to be in the space where the incident minibeams are sufficiently small (less than 0.7 mm) and are completely separated from (have not merged with) their neighbors.

The present methods can also be combined with radiation dose enhancement methods. For example, the lower beam energy of the orthovoltage x-rays makes the present method better suited and more effective than conventional MV methods for combining with tumor dose enhancement. This is because the orthovoltage x-ray photoelectric cross sections in the heavy elements used in contrast agents are significantly larger than the cross-section of MeV x-rays in those same elements. In embodiments, the methods described herein include the administration of dose-enhancing substances to the patient to radio-sensitize a tumor or other target. The agents may be of any suitable form, including nanoparticles, and may be comprised of one or more of iodine, gadolinium, gold, and platinum, with or without the use of active targeting methods, and drugs without or without encapsulation in liposomes or polymeric delivery vehicles. The tumor dose enhancement factor can be very large because of the large photoelectric cross section in those elements of x-rays in the orthovoltage energy range, i.e., 150 to 400 keV x-rays. In comparison, the photoelectric cross section of MeV is not very large at all.

Another advantage of the method and system of the present disclosure is that they are usable for low cost, durable and portable radiation therapy, requiring minimal training by locally trained healthcare staff. The system operation may be based on simple calibration, simple error diagnosis, and open source look-up tables. Further, the system may be configured to be operable in locations with limited or no infrastructure, simply with access to electricity, and have smaller shielding requirements by virtue of its lower beam energy. Accordingly, the system may be configured as a portable, mobile treatment system (possibly on a small truck) that can be used in low- and middle-income countries (LMICs) to treat targets of the central nervous system as well as other tumors with acceptable tissue depth, and may be preferable to MV therapeutic systems in such countries at least due to: a) the lower cost, probably by as much as 5-fold; b) portability; c) ease of use for treatment planning and operation, and d) smaller shielding requirements from the surrounding areas in the hospital of the present orthovoltage minibeam system and method.

In addition, the methods of the present disclosure are well-suited for treating thin tumors for which the relatively steep dose attenuation in tissues can be tailored to minimize the dose to the normal tissues located behind the tumor. An example for such clinical applications is the treatment of thyroid tumors.

The present methods are particularly well-suited for the treatment of brain tumors and, particularly, pediatric brain tumors due to their large tissue-sparing effects and low accumulated dose compared to other methods. The brain structures to which radiation damage, using other techniques, produces more significant effects include the hippocampus and the cortex. Radiation damage to the pediatric cortex has been related to the disturbance of the pediatric cortex's gliogenesis, a process producing neural progenitor cells; these cells later differentiate to produce new oligodendrocytes. Temporal lobes are another radiosensitive structure whose radiosensitivity is also much higher in children. Cognitive deficits can also be produced in patients, particularly children, due to the integral brain dose, i.e., the accumulated dose given in the entire brain.

The physical characteristics of both MV x-rays and proton beams impact the amount of radiation and the integral brain dose on the hippocampus and cortex. Although the MV x-rays have a sparing effect in the skin and other shallow tissues that could cover part of the cortex (FIG. 1), their dose distribution in the body is characterized by peaking early in the tissues, large dose penetration, and large lateral penumbra, which can produce significant dose to the cortex on the opposite side of the brain and to the temporal lobes. This dose distribution also produces a large integral brain dose. As for proton therapy, its lack of shallow-tissue-sparing effect could translate to excessive dose to the cortex. As a result, despite proton therapy's much better dose confinement to the target than the MV x-rays, it still produces cognitive deficits in both adults and children.

Compared to conventional radiation therapy methods, e.g., using MV x-rays, gamma rays, or protons, the methods of the present disclosure are particularly advantageous for treatment of tumors of the brain, head and neck, brainstem, spinal cord, spinal column and the like for numerous reasons. For example, the orthovoltage minibeams of the present disclosure produce smaller dose to the non-targeted tissues located distal to the target because of their lower beam energy, and they produce smaller dose to tissues located lateral to the tumor or target due to their smaller lateral penumbra, providing a tighter dose distribution. This results in smaller accumulative dose to the brain, while still maintaining tissue-sparing to the skin and both proximal and distal tissue.

Due to the tight dose distribution produced at the target by the orthovoltage x-rays, particularly due to the sharp lateral dose falloff described supra, the methods of the present disclosure are also ideal for treating neurological targets such as the epileptogenic foci. In contrast, the conventional methods of Gamma-Knife and stereotactic radiosurgery with MV x-rays produced by electron linacs produce a much larger amount of dose in the non-targeted tissues. The results are commonly an unacceptable amount of edema in the brain and unacceptable late radiation damage to the non-targeted brain. On the basis of the dosimetric advantages of the present methods over those employing high energy x-rays, the present methods provide a much more effective treatment for epilepsy than the conventional radiosurgery methods. The estimated factor of two in dose saving to the non-targeted tissues that would result with the use of orthovoltage x-ray minibeam treatment in accordance with the present methods is significant in increasing the method's efficacy by allowing the use of higher target doses and in reducing the edema and brain damage produced in the non-targeted brain.

The present methods can be used, for example, to treat focal epilepsy by producing radiation damage, including tissue necrosis, to the epileptogenic foci, with less damage to the surrounding brain compared to the method practiced today with MV x rays. The method can also be used to treat general epilepsy by produced radiation damage, including tissue necrosis, in certain brain structures.

In embodiments, methods further include applying the orthovoltage x-ray minibeam treatment of the present disclosure to the treatment of epilepsy, tumors including brain tumors, e.g., pediatric brain tumors, and tumors of the head and neck, brainstem, spinal cord, and spinal column.

While the disclosure has been particularly shown and described with reference to specific embodiments, it should be apparent to those skilled in the art that the foregoing is illustrative only and not limiting, having been presented by way of example only. Well-known functions or constructions are not described in detail to avoid obscuring the present disclosure in unnecessary detail. Various changes in form and detail may be made therein without departing from the spirit and scope of the disclosure. Therefore, numerous other embodiments are contemplated as falling within the scope of the present invention as defined by the accompanying claims and equivalents thereto.

What is claimed is:

1. A method for delivering therapeutic radiation to a target within a subject, wherein the target is located at a predetermined depth, the predetermined depth being measured from an irradiated portion of a surface of the skin of the subject, the method comprising:
   positioning a multi-aperture collimator within a trajectory of radiation produced by an x-ray source generating orthovoltage x-rays, the trajectory of orthovoltage x-rays being directed at the target, the multi-aperture collimator positioned and configured to generate an array of minibeams on the surface of the skin comprising slightly diverging spatially distinct minibeams having a predetermined center-center spacing between adjacent minibeams, and wherein a width of each minibeam is between about 0.1 mm and about 0.6 mm;
   irradiating the surface of the skin with the array of minibeams; and
   delivering an effective beam of therapeutic radiation to the target, said delivering including controlling a tissue depth from the irradiated surface of the skin at which the adjacent minibeams in the array merge sufficiently to form the effective beam of therapeutic radiation.

2. The method of claim 1, wherein the step of controlling includes forming the effective beam proximal to the target.

3. The method of claim 1, wherein controlling the tissue depth at which the adjacent minibeams merge sufficiently to form the effective beam includes adjusting at least one of the predetermined center-to-center spacing, the width, and a distance between the x-ray source and the multi-aperture collimator.

4. The method of claim 1, wherein delivering the effective beam of therapeutic radiation further includes sparing irradiated tissue proximal to the target from radiation damage, the tissue depth also corresponding to a tissue sparing depth.

5. The method of claim 1, further including limiting the width of the minibeams to be between about 0.25 mm and about 0.35 mm.

6. The method of claim 1, wherein the multi-aperture collimator is further configured such that the array of minibeams is a two-dimensional array of pencil minibeams, the width corresponding to a diameter of each pencil minibeam.

7. The method of claim 6, wherein a cross-sectional profile of each pencil minibeam is one of a round, elliptical, square, rectangular, and polygonal shape.

8. The method of claim 1, wherein the multi-aperture collimator is a multi-slit collimator configured with elongated slits such that the array of minibeams is an array of narrow and elongated planar minibeams.

9. The method of claim 8, the width corresponding to a thickness of each planar minibeam, the method further including limiting the width of each planar minibeam to a range of between about 0.25 mm to about 0.35 mm.

10. The method of claim 8, wherein the x-ray source has an elongated shape, the method further including aligning the elongated slits of the multi-slit collimator with the elongated shape of the x-ray source.

11. The method of claim 1, wherein controlling the tissue depth at which the adjacent minibeams merge sufficiently to form the effective beam includes adjusting a size of the x-ray source from which the orthovoltage x-rays are generated.

12. The method of claim 4, including varying the tissue depth from about 1 cm to about 10 cm, the tissue depth being based on a predetermined depth of the target from the surface of the skin.

13. The method of claim 1, including operating the x-ray tube in a range between about 100 kVp and about 500 kVp.

14. The method of claim 1, wherein the multi-aperture collimator includes a multi-aperture, heavy-metal plate.

15. The method of claim 1, wherein controlling the tissue depth includes selecting the width, the predetermined center-to-center spacing, and the distance between the x-ray source and the multi-aperture collimator such that each of the slightly diverging spatially distinct minibeams broaden to less than 1.0 mm in width before they merge to form the effective beam.

16. The method of claim 1, the method further comprising changing an angular position of the x-ray source and the trajectory of orthovoltage x-rays generated therefrom relative to the target such that the target is irradiated from a different direction, and repeating the positioning, the irradiating and the delivering step for the different direction and for irradiating a different portion of the skin with the array of minibeams generated by the multi-aperture collimator, the delivering step being repeated to deliver the effective beam of therapeutic radiation to the target from the different direction.

17. The method of claim 16, further comprising, for each angular position, adjusting a beam-shaping collimator positioned proximal to the multi-aperture array to conform a shape of the effective beam to a shape of the target based on the direction of the trajectory relative to the target.

18. The method of claim 1, the irradiating step further comprising generating an arc of radiation around the target from each of the minibeams in the array, the delivering step including merging adjacent arcs of radiation at the tissue depth to form the effective beam of therapeutic radiation.

19. The method of claim 18, wherein the minibeams are planar minibeams formed from elongated slits of a multi-slit collimator, each of the arcs of radiation being generated from the minibeams by rotating the x-ray source together with the multi-slit collimator, such that the arcs are generated around the target in planes parallel to the elongated slits of the multi-slit collimator.

20. The method of claim 18, further comprising adjusting a shape and an intensity of a source beam comprising the orthovoltage x-rays generated by the x-ray source to conform the effective beam of therapeutic radiation to a shape of the target based on a direction from which the effective beam irradiates the target, the method further comprising continuously adjusting the distance between the x-ray source and the multi-aperture collimator to maintain the tissue depth, at which the arcs formed from the minibeams merge to form the effective beam of therapeutic radiation, to be proximal to the target.

21. The method of claim 1, the method further comprising administering dose-enhancing agents to the subject prior to the irradiating step to radio-sensitize the target.

22. The method of claim 21, wherein the agents include one or more of iodine, gadolinium, gold, and platinum.

23. The method of claim 21, wherein the agents are encapsulated in one of liposomes or polymeric delivery vehicles.

24. The method of claim 1, wherein the target encompasses one of a tumor and an epileptogenic foci.

25. A system for delivering therapeutic radiation to a target volume within a subject, wherein the target is located at a predetermined depth, the predetermined depth being measured from an irradiated portion of the skin of the subject, the system comprising:
an x-ray source generating orthovoltage x-rays; and
a multi-aperture collimator, the multi-aperture collimator being configured for positioning on or near the skin and within a trajectory of the orthovoltage x-rays generated from the x-ray source, the trajectory of orthovoltage x-rays being directed at the target, the multi-aperture collimator comprising an array of apertures having a width of between about 0.1 mm and about 0.6 mm and a predetermined center-center spacing to generate an array of slightly diverging spatially distinct minibeams of the orthovoltage x-rays at the skin,
wherein the width and the predetermined center-center spacing of the multi-aperture collimator, a size of the x-ray source, and a distance between the x-ray source and the multi-aperture collimator are configured to deliver an effective beam of therapeutic radiation to the target, the effective beam being formed by sufficient merging of the adjacent minibeams in the array proximal to the target.

26. The system of claim 25, wherein the width, the predetermined center-center spacing, the size and the distance are configured to form the effective beam of therapeutic radiation proximal to the target.

27. The system of claim 25, wherein the multi-aperture collimator is removably interchangeable, the system further comprising a set of multi-aperture collimators configured with predefined aperture widths and shapes and predefined center-center spacings.

28. The system of claim 25, wherein the system is portable and configured to be transported on and operated from a mobile platform.

29. The system of claim 25, wherein the width of the multi-aperture collimator is between about 0.25 mm and about 0.35 mm.

30. The system of claim 25, wherein the multi-aperture collimator is further configured such that the array of minibeams is a two-dimensional array of pencil minibeams, the width corresponding to a diameter of each pencil minibeam, wherein the diameter is a range of between about 0.25 mm and about 0.35 mm.

31. The system of claim 30, wherein a cross-sectional profile of each pencil minibeam is one of a round, elliptical, square, rectangular, and polygonal shape.

32. The system of claim 25, wherein the multi-aperture collimator is a multi-slit collimator configured with elongated slits such that the array of minibeams is an array of narrow and elongated planar minibeams.

33. The system of claim 25, wherein the orthovoltage x-ray tube operates in a range between about 100 kVp and about 500 kVp.

34. The system of claim 25, wherein the multi-aperture collimator is a multi-aperture, heavy-metal collimator plate.

35. The system of claim 25, wherein the width, the predetermined center-to-center spacing, and the distance between the x-ray source and the multi-aperture collimator are configured such that each of the slightly diverging spatially distinct minibeams broaden to less than 1.0 mm in width before merging to form the effective beam of therapeutic radiation.

36. The system of claim 25, further comprising a beam-shaping collimator positioned within the trajectory of x-rays and proximal to the multi-aperture collimator, the beam-shaping collimator configured to be adjustable to conform the effective beam of therapeutic radiation to a shape and size of the target.

37. The system of claim 36, further comprising a rotatable and translatable gantry on which the x-ray source, the beam-shaping collimator and the multi-aperture collimator are mounted, the gantry being positioned and configured to be rotatable around a horizontal platform on which a subject being treated is located, the gantry being configured to position the target in the trajectory of the orthovoltage x-rays, wherein the gantry is further configured to tilt around a vertical axis to the platform to change a direction from which the target is irradiated with the effective beam of therapeutic radiation, and to rotate around a longitudinal axis of the horizontal platform to generate arcs of radiation from each of the minibeams.

38. The system of claim 37, the system further configured to continuously adjust the beam-shaping collimator to conform the effective beam to the shape and size of the target based on the direction of irradiation as the gantry is tilted and rotated, and to continuously adjust the distance between the x-ray source and the multi-aperture collimator to maintain the tissue depth at which the effective beam is formed to be proximal to the target.

39. A method for delivering therapeutic radiation to a target within a subject, wherein the target is located at a predetermined depth, the predetermined depth being measured from an irradiated portion of a surface of the skin of the subject, the method comprising:
positioning a multi-aperture collimator within a trajectory of orthovoltage x-rays generated by an orthovoltage x-ray source, the trajectory of orthovoltage x-rays being directed at the target, the multi-aperture collimator positioned and configured to generate an array of minibeams on the surface of the skin comprising slightly diverging spatially distinct minibeams having a predetermined width and a predetermined center-center spacing between adjacent minibeams;
irradiating the surface of the skin with arcs of radiation formed from the array of minibeams, irradiating further comprising generating the arcs of radiation around the target from the minibeams in the array; and
delivering an effective beam of therapeutic radiation to the target, said delivering including controlling a tissue depth from the irradiated surface of the skin at which adjacent arcs of radiation formed from the adjacent minibeams in the array merge to form the effective beam of therapeutic radiation.

40. The method of claim 39, including limiting the width of the minibeams to be between about 0.1 mm and about 0.6 mm.

41. The method of claim 39, wherein the minibeams are planar minibeams formed from elongated slits of a multi-slit collimator, each of the arcs of radiation being generated from the minibeams by rotating the x-ray source together with the multi-slit collimator, such that the arcs are generated around the target in planes parallel to the elongated slits of the multi-slit collimator.

42. The method of claim 39, further comprising adjusting a shape and an intensity of the effective beam of therapeutic radiation to conform to a shape of the target based on a direction from which the beam irradiates the target.

43. The method of claim 42, further comprising continuously adjusting the distance between the orthovoltage x-ray source and the multi-aperture collimator to maintain the tissue depth, at which the minibeams forming the arcs of radiation merge sufficiently to form the effective beam, to be proximal to the target.

* * * * *